United States Patent
Huang et al.

(10) Patent No.: US 11,401,356 B2
(45) Date of Patent: Aug. 2, 2022

(54) OLEFIN POLYMERIZATION CATALYST COMPRISING CYCLOTRIVERATRYLENE AND DERIVATIVES THEREOF

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION

(72) Inventors: Ting Huang, Beijing (CN); Zifang Guo, Beijing (CN); Zhufang Sun, Beijing (CN); Junling Zhou, Beijing (CN); Lunjia Xie, Beijing (CN); Hongxu Yang, Beijing (CN); Bingyi Li, Beijing (CN); Qingqiang Gou, Beijing (CN); Tingjie Huang, Beijing (CN); Peng Kou, Beijing (CN); Xiaofan Zhang, Beijing (CN); Meiyan Fu, Beijing (CN); Jie Lin, Beijing (CN); Yonghua Ma, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(*) Notice: Subject to any disclaimer, the term of this patent is extended or adjusted under 35 U.S.C. 154(b) by 298 days.

(21) Appl. No.: 16/631,482

(22) PCT Filed: Jul. 19, 2018

(86) PCT No.: PCT/CN2018/096248
§ 371 (c)(1),
(2) Date: Jan. 16, 2020

(87) PCT Pub. No.: WO2019/015638
PCT Pub. Date: Jan. 24, 2019

(65) Prior Publication Data
US 2020/0181296 A1    Jun. 11, 2020

(30) Foreign Application Priority Data

Jul. 19, 2017  (CN) .......................... 201710591148.0
Jul. 19, 2017  (CN) .......................... 201710591173.9
(Continued)

(51) Int. Cl.
*C08F 10/02*       (2006.01)
*C08F 4/609*       (2006.01)
(Continued)

(52) U.S. Cl.
CPC .............. *C08F 10/02* (2013.01); *C07C 43/21* (2013.01); *C07C 43/225* (2013.01); *C08F 10/06* (2013.01);
(Continued)

(58) Field of Classification Search
USPC ....................................................... 526/125.6
See application file for complete search history.

(56) References Cited

U.S. PATENT DOCUMENTS 4,018,832 A      4/1977  Hyatt
2016/0347880 A1  12/2016 Bantu et al.

FOREIGN PATENT DOCUMENTS

CN      1330086 A     1/2002
CN      1726230 A     1/2006
(Continued)

OTHER PUBLICATIONS

Tetrahedon Report 226, Tetrahedron, vol. 43., No. 24, pp. 5725-5759 (1987).
Kemp, Richard A.et al., "Calixarenes as a new class of external electron donors in Ziegler-Natta polypropylene catalysts," Journal of Molecular Catalysis A: Chemical, vol. 149, pp. 125-133 (1999).
Science in China Series B: Chemistry, vol. 39, No. 4, pp. 329-342 (2009).
(Continued)

*Primary Examiner* — Fred M Teskin
(74) *Attorney, Agent, or Firm* — Finnegan, Henderson, F Arabow, Garrett & Dunner LLP

(57) ABSTRACT

The present invention discloses a Ziegler-Natta catalyst system for olefin polymerization, comprising at least one compound represented by formula (I) as (i) an internal electron donor, (ii) an external electron donor, or (iii) the both, wherein $M_1$, $M_2$, $M_3$, $M_4$, $M_5$, $M_6$, $M_1'$, $M_2'$, $M_3'$, $M_4'$, $M_5'$ and $M_6'$ are each independently selected from the group consisting of hydrogen, hydroxy, amino, aldehyde group, carboxy, acyl, halogen atoms, $-R_1$ and $-OR_2$, wherein $R_1$ and $R_2$ are each independently a $C_1$-$C_{10}$ hydrocarbyl, which is unsubstituted or substituted by a substituent selected from the group consisting of hydroxy, amino, aldehyde group, carboxy, acyl, halogen atoms, $C_1$-$C_{10}$ alkoxy and heteroatoms; and wherein, when among $M_1$-$M_6$ and $M_1'$-$M_6'$, any two adjacent groups on the same phenyl ring are each independently selected from the group consisting of $R_1$ and $-OR_2$, the two adjacent groups may optionally be linked to form a ring, with a proviso that $M_1$, $M_2$, $M_3$, $M_4$, $M_5$, $M_6$, $M_1'$, $M_2'$, $M_3'$, $M_4'$, $M_5'$ and $M_6'$ are not simultaneously hydrogen.

Formula (I)

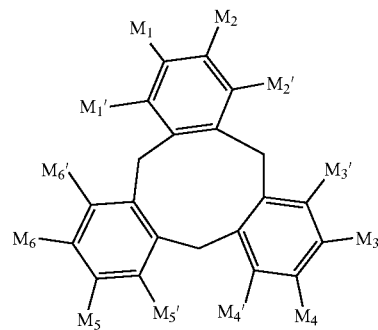

33 Claims, No Drawings

| (30) | Foreign Application Priority Data | | |
|---|---|---|---|
| Jul. 19, 2017 | (CN) | ................ | 201710591181.3 |
| Jul. 19, 2017 | (CN) | ................ | 201710591855.X |
| Jul. 19, 2017 | (CN) | ................ | 201710591859.8 |
| Jul. 19, 2017 | (CN) | ................ | 201710592381.0 |
| Jul. 19, 2017 | (CN) | ................ | 201710592383.X |
| Jul. 19, 2017 | (CN) | ................ | 201710592384.4 |
| Jul. 19, 2017 | (CN) | ................ | 201710592385.9 |
| Jul. 19, 2017 | (CN) | ................ | 201710592386.3 |
| Jul. 19, 2017 | (CN) | ................ | 201710592398.6 |

(51) Int. Cl.
  *C07C 43/21* (2006.01)
  *C07C 43/225* (2006.01)
  *C08F 10/06* (2006.01)
(52) U.S. Cl.
  CPC ...... *C07C 2603/40* (2017.05); *C08F 2410/01* (2013.01)

(56) References Cited

FOREIGN PATENT DOCUMENTS

| CN | 1743347 A | 3/2006 |
| CN | 1798774 A | 7/2006 |
| CN | 1958620 A | 5/2007 |
| CN | 101050248 A | 10/2007 |
| CN | 102295717 A | 12/2011 |
| CN | 102453057 A | 5/2012 |
| CN | 102807638 A | 12/2012 |
| CN | 103772536 A | 5/2014 |

OTHER PUBLICATIONS

Song, Jing-Ru et al., "Synthesis of functionalized cyclotriveratrylene analogues with C1-symmetry and the application for 1,4-Michael addition of alcohols to unsaturated aryl ketone," Tetrahedron, vol. 69, pp. 7308-7313 (2013).

International Search Report for International Application No. PCT/CN2018/096248, dated Sep. 29, 2018.

OLEFIN POLYMERIZATION CATALYST COMPRISING CYCLOTRIVERATRYLENE AND DERIVATIVES THEREOF

CROSS REFERENCE TO RELATED APPLICATIONS

This application is a national stage filing under 35 U.S.C. § 371 of International Application No. PCT/CN2018/096248, filed Jul. 19, 2018, and claims the priority benefit of Chinese Patent Application Nos. 201710591148.0, 201710591173.9, 201710591181.3, 201710591855.X, 201710591859.8, 201710592381.0, 201710592383.X, 201710592384.4, 201710592385.9, 201710592386.3, 201710592398.6, filed Jul. 19, 2017, which are incorporated herein by reference in their entireties.

FIELD

The present disclosure belongs to the field of olefin polymerization catalysts, and specifically to olefin polymerization catalysts comprising cyclotriveratrylene or a derivative thereof.

BACKGROUND

In the field of olefin polymerization catalysts, it has always been attempted to introduce various electron donors into olefin polymerization catalysts to improve one or more properties of the catalysts. For example, CN1958620A, CN1743347A, CN102295717A and CN103772536A teach, respectively, to introduce a siloxane-type electron donor, a mixed electron donor of an o-alkoxybenzoate and a carboxylate (or a diether), and a benzoate-type electron donor into a catalyst in order to improve the hydrogen response of the catalyst. For another example, CN1726230A, CN1798774A and CN101050248A teach to introduce an electron donor such as alcohol, ketone, amine, amide, nitrile, alkoxysilane, aliphatic ether, aliphatic carboxylate and the like into a catalyst to improve the copolymerization property of the catalyst. For another example, CN102807638A teaches to introduce a mixed electron donor of a long-carbon-chain monoester and a short-carbon-chain monoester into a catalyst to enhance the activity of the catalyst.

Cyclotriveratrylene and some derivatives thereof are known (see, for example, Tetrahedron, Vol. 43, No. 24, pp. 5725-5759, 1987; Science in China Series B: Chemistry, Vol. 39, No. 4, pp. 329-342, 2009). However, the prior art has never taught to use the cyclotriveratrylene and derivatives thereof in an olefin polymerization catalyst.

SUMMARY OF THE INVENTION

The present inventors have surprisingly found in studies that: when cyclotriveratrylene or a derivative thereof is introduced, as an internal electron donor, into a solid catalyst component of an olefin polymerization catalyst system, the olefin polymerization catalyst can exhibit good copolymerization property and activity, but also can exhibit high polymerization activity and high polymer melt index under polymerization condition of high hydrogen gas-ethylene ratio (for example, hydrogen gas partial pressure/ethylene partial pressure ≥1.5); and, when the heteroatom-containing cyclotriveratrylene or a derivative thereof is introduced, as an external electron donor, into an olefin polymerization catalyst system, the catalyst system exhibits good copolymerization property. Based on these findings, the present inventions have been made.

A first aspect of the present disclosure provides use of cyclotriveratrylene and derivatives thereof in olefin polymerization catalysts, the cyclotriveratrylene and derivatives thereof having a structure represented by formula (I):

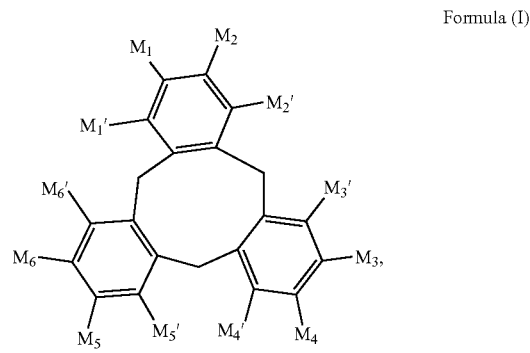

Formula (I)

wherein $M_1$, $M_2$, $M_3$, $M_4$, $M_5$, $M_6$, $M_1'$, $M_2'$, $M_3'$, $M_4'$, $M_5'$, $M_6'$ are each independently selected from the group consisting of hydrogen, hydroxy, amino, aldehyde group, carboxy, acyl, halogen atoms, —$R_1$ or —$OR_2$, wherein $R_1$ and $R_2$ are each independently a $C_1$-$C_{10}$ hydrocarbyl, which is unsubstituted or substituted by a substituent selected from hydroxy, amino, aldehyde group, carboxy, acyl, halogen atoms, $C_1$-$C_{10}$ alkoxy and heteroatoms; wherein when, among $M_1$-$M_6$ and $M_1'$-$M_6'$, any two adjacent groups on the same phenyl ring, for example, $M_1$ and $M_1'$, $M_1$ and $M_2$, $M_2$ and $M_2'$, $M_3$ and $M_3'$, $M_3$ and $M_4$, $M_4$ and $M_4'$, $M_5$ and $M_5'$, $M_5$ and $M_6$, $M_6$ and $M_6'$, are each independently selected from the group consisting of $R_1$ and —$OR_2$, the two adjacent groups may optionally be linked to form a ring, with a proviso that $M_1$, $M_2$, $M_3$, $M_4$, $M_5$, $M_6$, $M_1'$, $M_2'$, $M_3'$, $M_4'$, $M_5'$, $M_6'$ are not simultaneously hydrogen.

In an embodiment, the structure of the cyclotriveratrylene and derivatives thereof is represented by formula (I'):

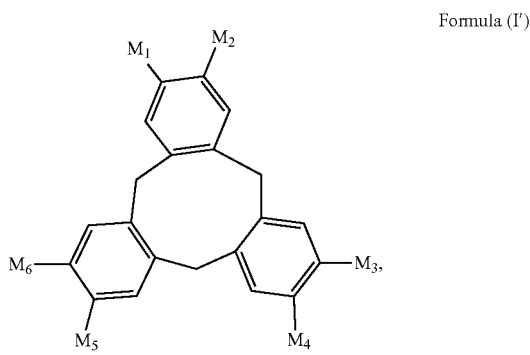

Formula (I')

wherein $M_1$, $M_2$, $M_3$, $M_4$, $M_5$ and $M_6$ are each independently selected from the group consisting of hydrogen, hydroxy, amino, aldehyde group, carboxy, acyl, halogen atoms, —$R_1$ and —$OR_2$, wherein $R_1$ and $R_2$ are each independently a $C_1$-$C_{10}$ hydrocarbyl, which is unsubstituted or substituted by a substituent selected from hydroxy, amino, aldehyde group, carboxy, acyl, halogen atoms, $C_1$-$C_{10}$ alkoxy and heteroatoms, with a proviso that when two adjacent groups on the same phenyl ring, $M_1$ and $M_2$, or $M_3$ and $M_4$, or $M_5$ and $M_6$, are each independently selected from the group consisting of —$R_1$ and —$OR_2$, the two adjacent groups may optionally be linked to form a ring, and with a proviso that $M_1$, $M_2$, $M_3$, $M_4$, $M_5$ and $M_6$ are not simultaneously hydrogen.

A second aspect of the present disclosure provides a catalyst system for olefin polymerization, comprising at least one compound represented by the above-described formula (I) or (I') as (i) an internal electron donor, (ii) an external electron donor, or (iii) the both.

In a subaspect of the second aspect, the present disclosure provides a solid catalyst component for olefin polymerization, which is at least one of the followings:

1) a solid catalyst component comprising magnesium, titanium, halogen and an internal electron donor compound, wherein the internal electron donor compound comprises at least one compound represented by the above-described formula (I) or (I');

2) a solid catalyst component comprising a reaction product of: a magnesium halide-alcohol adduct, a titanium compound, an internal electron donor compound, and an optional organic aluminum compound, wherein the internal electron donor compound comprises at least one compound represented by the above-described formula (I) or (I');

3) a solid catalyst component comprising a reaction product of: an alkoxy magnesium compound, a titanium compound and an internal electron donor compound, wherein the internal electron donor compound comprises at least one compound represented by the above-described formula (I) or (I');

4) a solid catalyst component comprising a reaction product of: a finely-divided support having a particle size of from 0.01 to 10 microns, a magnesium halide, a titanium halide and an internal electron donating compound, wherein the internal electron donating compound comprises an internal electron donor a and an internal electron donor b, the internal electron donor a being at least one compound represented by the above-described formula (I) or (I'); and the internal electron donor b being at least one selected from the group consisting of alkyl esters of $C_2$-$C_{10}$ saturated aliphatic carboxylic acids, alkyl esters of $C_7$-$C_{10}$ aromatic carboxylic acids, $C_2$-$C_{10}$ aliphatic ethers, $C_3$-$C_{10}$ cyclic ethers, and $C_3$-$C_{10}$ saturated aliphatic ketones;

5) a solid catalyst component comprising a reaction product of:

5-1) a magnesium-containing liquid component, which is at least one selected from the following components:

i) an alkyl magnesium or a solution thereof in a liquid hydrocarbon, the alkyl magnesium being of general formula $MgR_1R_2$, where $R_1$ and $R_2$ are each independently selected from the group consisting of $C_1$-$C_{10}$ hydrocarbyl groups, which are unsubstituted or substituted by a substituent selected from the group consisting of hydroxy, amino, aldehyde group, carboxy, halogen atoms, alkoxy and heteroatoms;

ii) a product obtained by dissolving, in a solvent system comprising an organophosphorus compound, an organic epoxy compound and an optional alcohol compound $R_5OH$, a magnesium dihalide or a derivative deriving from a magnesium dihalide by replacing one halogen atom in the molecular formula of the magnesium dihalide with group $R_3$ or $OR_4$; and iii) a product obtained by dispersing a magnesium dihalide or a derivative deriving from a magnesium dihalide by replacing one halogen atom in the molecular formula of the magnesium dihalide with group $R_3$ or $OR_4$ in an alcohol compound $R_5OH$;

wherein $R_3$, $R_4$ and $R_5$ are each independently selected from the group consisting of $C_1$-$C_{10}$ hydrocarbyl groups, which are unsubstituted or substituted by a substituent selected from the group consisting of hydroxy, amino, aldehyde group, carboxy, halogen atoms, alkoxy and heteroatoms;

5-2) a titanium compound;

5-3) an internal electron donor compound, the internal electron donor compound comprising at least one compound represented by the above-described formula (I) or (I'); and optionally, 5-4) an auxiliary precipitant, which is selected from the group consisting of organic anhydride compounds and/or organic silicon compounds.

In another subaspect of the second aspect, the present disclosure provides an olefin polymerization catalyst comprising a reaction product of:

1) the above-described solid catalyst component;

2) a cocatalyst, for example, an organic aluminum compound; and 3) an optional external electron donor compound.

In another subaspect of the second aspect, the present disclosure provides an olefin polymerization catalyst comprising a reaction product of:

1) a solid catalyst component comprising magnesium, titanium, halogen and an optional internal electron donor compound;

2) a cocatalyst, for example, an organic aluminum compound; and 3) an external electron donor compound;

wherein the external electron donor compound comprises at least one compound represented by the above-described formula (I) or (I').

In some embodiments of this subaspect, the solid catalyst component comprises a reaction product of: a magnesium halide-alcohol adduct, a titanium compound, an optional internal electron donor compound and an optional organic aluminum compound; preferably, the organic aluminum compound is of general formula $AlR^3{}_aX^3{}_bH_c$, where $R^3$ is a $C_1$-$C_{14}$ hydrocarbyl; $X^3$ is a halogen atom, preferably Cl, Br or I; each a, b and c is a number of from 0 to 3, and a+b+c=3.

In some embodiments of this subaspect, the solid catalyst component comprises a reaction product of: an alkoxy magnesium compound, a titanium compound and an optional internal electron donor compound.

In some embodiments of this subaspect, the solid catalyst component comprises a reaction product of: a finely-divided support, a magnesium halide, a titanium halide, an internal electron donor b and an optional internal electron donor a;

wherein the internal electron donor b is at least one selected from the group consisting of alkyl esters of $C_2$-$C_{10}$ saturated aliphatic carboxylic acids, alkyl esters of $C_7$-$C_{10}$ aromatic carboxylic acids, $C_2$-$C_{10}$ aliphatic ethers, $C_3$-$C_{10}$ cyclic ethers, and $C_3$-$C_{10}$ saturated aliphatic ketones; and wherein the optional internal electron donor a is at least one compound represented by the above-described formula (I) or (I').

In some embodiments of this subaspect, the solid catalyst component comprises a reaction product of: a magnesium-containing liquid component, a titanium compound, an optional internal electron donor compound and an optional auxiliary precipitant, wherein the auxiliary precipitant is selected from the group consisting of organic anhydride compounds and/or organic silicon compounds.

A third aspect of the present disclosure provides use of the above-described olefin polymerization catalyst in olefin polymerization reactions.

A fourth aspect of the present disclosure provides an olefin polymerization process comprising: contacting an olefin monomer and an optional comonomer with the above-described olefin polymerization catalyst under polymerization conditions to form a polyolefin product and recovering the polyolefin product. In some embodiments, the process comprises contacting ethylene and an optional comonomer such as a C3-C12 α-olefin with the above-described olefin polymerization catalyst under polymerization conditions to form a polyethylene product and recovering the polyethylene product. In other embodiments, the process comprises contacting propylene and an optional comonomer such as ethylene or a C4-C12 α-olefin with the above-described olefin polymerization catalyst under polymerization conditions to form a polypropylene product and recovering the polypropylene product.

A fifth aspect of the present disclosure provides polyolefin products, for example, polyethylenes or polypropylenes, obtainable by the above-described olefin polymerization process.

According to the present disclosure, the cyclotriveratrylene and derivatives thereof represented by the formula (I)/(I') can be used as an internal electron donor and/or an external electron donor in Ziegler-Natta-type olefin polymerization catalysts. The incorporation of the cyclotriveratrylene and derivatives thereof into the olefin polymerization catalysts can improve the performance of the resultant catalysts, for example, activity, hydrogen response and copolymerization property.

DETAILED DESCRIPTION OF THE PREFERRED EMBODIMENTS

Various specific embodiments of the present disclosure will now be described. It will be appreciated that the specific embodiments described herein are only to illustrate and explain the present disclosure, but not to limit the present disclosure.

Definitions

As used herein, each of the terms "a", "an", and "the" in the singular forms may also refer to and include the plural reference or object, unless specifically otherwise defined or stated therein, or unless the context clearly indicates otherwise.

All numerical values within the detailed description and the claims herein are modified by "about" or "approximately" the indicated value and consider experimental error and variations that would be expected by a person having ordinary skill in the art, for example, ±10%, or ±5%, or ±2%, or ±1%.

For the purpose of the present disclosure and the appended claims, an olefin present in a polymer is a polymerized form of the olefin. Likewise, the use of the term polymer is intended to encompass homopolymer and copolymer, wherein the copolymer encompasses any polymer having two or more chemically different monomers.

The term "polyolefin" means a polymer containing olefin-derived repeating units, for example, poly-α-olefin, such as polypropylene and/or polyethylene.

"Polypropylene" means a polyolefin containing propylene-derived repeating units, including polypropylene homopolymers and polypropylene copolymers in which at least 50%, preferably at least 85% (by number) of the repeating units are derived from propylene monomer. In the context, polypropylene, propylene polymer and polypropylene polymer are used interchangeably.

"Polyethylene" means a polyolefin containing ethylene-derived repeating units, including polyethylene homopolymers and polyethylene copolymers in which at least 50%, preferably at least 85% (by number) of the repeating units are derived from ethylene monomer. In the context, polyethylene, ethylene polymer and polyethylene polymer are used interchangeably.

"Copolymer" means a polymer containing repeating units deriving from at least two different monomers, the monomers being preferably, for example, olefins such as ethylene, propylene, butenes and the like. Thus, a propylene copolymer or propylene-based polymer contains at least two different monomers, wherein more than 50%, preferably more than 85% (by number) of the repeating units are derived from propylene monomer.

"Terpolymer" means a polymer containing repeating units deriving from at least three different monomers, the monomers being preferably, for example, olefins such as ethylene, propylene, butenes and the like. Thus, a propylene terpolymer contains at least three different monomers, wherein more than 50%, preferably more than 85% (by number) of the repeating units are derived from propylene monomer.

An "olefin", alternatively referred to as "alkene", is a linear, branched, or cyclic compound of carbon and hydrogen having at least one double bond. An "α-olefin" is an olefin having a double bond on α (or 1-) position.

In the context, "catalyst" and "catalyst system" are used interchangeably. The "catalyst" is a combination of at least one solid catalyst component, at least one cocatalyst and an optional external electron donor component. A "polyolefin" catalyst is a catalyst system that can polymerize olefin monomer(s) into a polymer.

As used herein, the term "hydrocarbyl" means a group that may be derived from a hydrocarbon by removing one or more hydrogen atoms from its chemical formula, and encompasses linear, branched or cyclic alkyl, linear, branched or cyclic alkenyl, linear, branched or cyclic alkynyl, aryl, aralkyl, and alkaryl. Unless specified otherwise, as used herein, the term "hydrocarbyl" generally refers to a hydrocarbyl having 1 to 30, preferably 1 to 20, more preferably 1 to 10, and still more preferably 1 to 6 carbon atoms.

"Alkyl" means a paraffinic hydrocarbyl that may be derived from an alkane by removing one or more hydrogen atoms from its chemical formula. Unless specified otherwise, as used herein, the term "alkyl" generally refers to an alkyl having 1 to 30, preferably 1 to 20, more preferably 1 to 10, and still more preferably 1 to 6 carbon atoms, for example, methyl, ethyl or the like. Non-limiting examples of $C_1$-$C_{10}$ alkyl include: methyl, ethyl, n-propyl, isopropyl, n-butyl, sec-butyl, isobutyl, tert-butyl, n-pentyl, isopentyl, tert-pentyl, neo-pentyl, n-hexyl, n-heptyl, n-octyl, n-decyl, cyclopropyl, cyclopentyl, cyclohexyl, 4-methyl-cyclohexyl, 4-ethyl-cyclohexyl, 4-n-propyl-cyclohexyl and 4-n-butyl-cyclohexyl.

"Alkenyl" means an olefinic hydrocarbyl that may be derived from an alkene by removing one or more hydrogen atoms from its chemical formula. Unless specified otherwise, as used herein, the term "alkenyl" generally refers to an alkenyl having 2 to 30, preferably 2 to 20, more preferably 2 to 10, and still more preferably 2 to 6 carbon atoms. Examples of $C_2$-$C_{10}$ alkenyl include, but are not limited to, ethenyl, propenyl and allyl.

"Alkynyl" means an acetylenic hydrocarbyl that may be derived from an alkyne by removing one or more hydrogen atoms from its chemical formula. Unless specified otherwise, as used herein, the term "alkynyl" generally refers to an alkynyl having 2 to 30, preferably 2 to 20, more preferably 2 to 10, and still more preferably 2 to 6 carbon atoms. Examples of $C_2$-$C_{10}$ alkynyl include, but are not limited to, acetylenyl, propynyl and propargyl.

"Aryl" means an aromatic group that may be derived from an aromatic hydrocarbon such as benzene, naphthalene, phenanthrene, anthracene and the like by removing one or more hydrogen atoms from its chemical formula, for example, phenyl, naphthyl or the like. Examples of $C_6$-$C_{10}$ aryl include, but are not limited to, phenyl and naphthyl.

Examples of $C_7$-$C_{10}$ alkaryl include, but are not limited to, 4-methylphenyl and 4-ethylphenyl.

Examples of $C_7$-$C_{10}$ aralkyl include, but are not limited to, phenylmethyl, 2-phenylethyl, 3-phenyl-n-propyl, 4-phenyl-n-butyl, 2-dimethyl-2-phenyl-propyl and 2-phenylpropyl.

Unless specified otherwise, as used herein, the term "halogen atom" means F, Cl, Br or I.

Unless specified otherwise, as used herein, the term "heteroatom" means halogen atoms, O, N, S, P, Si, B and the like.

Unless specified otherwise, as used herein, the term "substituted $C_1$-$C_{10}$ hydrocarbyl" generally means that a hydrogen atom (preferably one hydrogen atom) and/or a carbon atom on the "$C_1$-$C_{10}$ hydrocarbyl" are/is substituted by a substituent. Preferably, the substituent is selected from the group consisting of hydroxy, amino, aldehyde group, carboxy, acyl, halogen atoms, alkoxy and heteroatoms.

Unless specified otherwise, as used herein, the term "amino" means $NR_1R_2$, where $R_1$ and $R_2$ may be selected from the group consisting of hydrogen atom or $C_1$-$C_{10}$ hydrocarbyl, and $R_1$ and $R_2$ may be identical or different.

In a first aspect, the present disclosure provides use of cyclotriveratrylene and derivatives thereof represented by formula (I) in olefin polymerization catalysts:

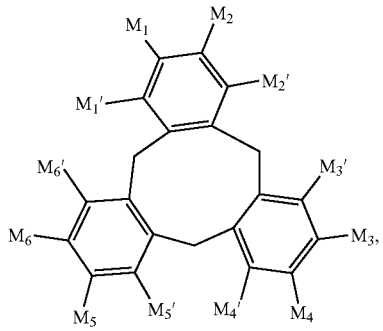

Formula (I)

wherein $M_1$, $M_2$, $M_3$, $M_4$, $M_5$, $M_6$, $M_1'$, $M_2'$, $M_3'$, $M_4'$, $M_5'$, $M_6'$, which are identical or different, are each selected from the group consisting of hydrogen, hydroxy, amino, aldehyde group, carboxy, acyl, halogen atoms, —$R_1$ and —$OR_2$, wherein $R_1$ and $R_2$ are each independently a $C_1$-$C_{10}$ hydrocarbyl, which is unsubstituted or substituted by a substituent selected from the group consisting of hydroxy, amino, aldehyde group, carboxy, acyl, halogen atoms, alkoxy and heteroatoms; wherein, when any two adjacent groups on the same phenyl ring such as $M_1$ and $M_1'$, $M_1$ and $M_2$, $M_2$ and $M_2'$, $M_3$ and $M_3'$, $M_3$ and $M_4$, $M_4$ and $M_4'$, $M_5$ and $M_5'$, $M_5$ and $M_6$, $M_6$ and $M_6'$ are each independently selected from the group consisting of $R_1$ and —$OR_2$, the two adjacent groups may optionally be linked to form a ring, with a proviso that $M_1$, $M_2$, $M_3$, $M_4$, $M_5$, $M_6$, $M_1'$, $M_2'$, $M_3'$, $M_4'$, $M_5'$, $M_6'$ are not simultaneously hydrogen.

Preferably, the cyclotriveratrylene and derivatives thereof are represented by formula (I'):

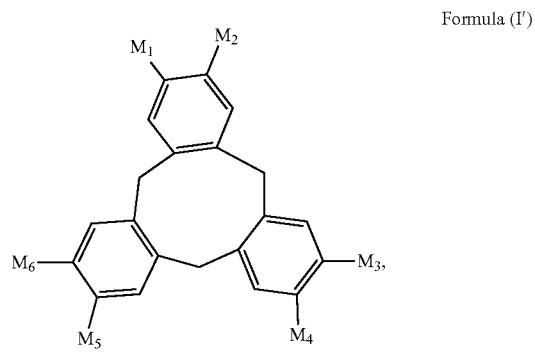

Formula (I')

wherein $M_1$, $M_2$, $M_3$, $M_4$, $M_5$ and $M_6$, which are identical or different, are each selected from the group consisting of hydrogen, hydroxy, amino, aldehyde group, carboxy, acyl, halogen atoms, —$R_1$ and —$OR_2$, wherein $R_1$ and $R_2$ are each independently substituted or unsubstituted $C_1$-$C_{10}$ hydrocarbyl, with the substituent being selected from the group consisting of hydroxy, amino, aldehyde group, carboxy, acyl, halogen atoms, alkoxy and heteroatoms;

when the two adjacent groups on the same phenyl ring, i.e., $M_1$ and $M_2$, or $M_3$ and $M_4$, or $M_5$ and $M_6$, are each independently selected from the group consisting of —$R_1$ and —$OR_2$, the two adjacent groups may optionally be linked to each other to form a cyclic structure, with a proviso that $M_1$, $M_2$, $M_3$, $M_4$, $M_5$ and $M_6$ are not simultaneously hydrogen.

According to the present disclosure, the $C_1$-$C_{10}$ hydrocarbyl may be selected from the group consisting of $C_1$-$C_{10}$ alkyl, $C_3$-$C_{10}$ cycloalkyl, $C_2$-$C_{10}$ alkenyl, $C_2$-$C_{10}$ alkynyl, $C_6$-$C_{10}$ aryl, $C_7$-$C_{10}$ alkaryl and $C_7$-$C_{10}$ aralkyl and the like.

Preferably, in the formula (I'), $M_1$, $M_2$, $M_3$, $M_4$, $M_5$ and $M_6$ are identical or different, and are each selected from the group consisting of hydroxy, amino, aldehyde group, halogen atoms, —$R_1$ and —$OR_2$, and $R_1$ and $R_2$ are each independently selected from the group consisting of unsubstituted or halogen-substituted $C_1$-$C_{10}$ hydrocarbyl groups.

In some embodiments, $M_1$, $M_3$ and $M_5$ are the same, and $M_2$, $M_4$ and $M_6$ are the same.

In some embodiments, $M_1$, $M_2$, $M_3$, $M_4$, $M_5$ and $M_6$ are the same.

In some preferred embodiments, the cyclotriveratrylene and derivatives thereof are at least one selected from the group consisting of compounds of formula (I):

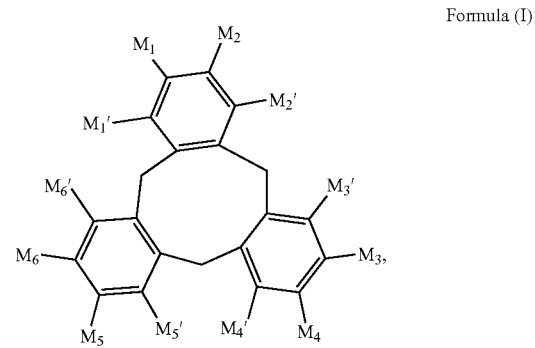

Formula (I)

Compound A: $M_1=M_2=M_3=M_4=M_5=M_6=OCH_3$, $M_1'=M_2'=M_3'=M_4'=M_5'=M_6'=H$;
Compound B: $M_1=M_2=M_3=M_4=M_5=M_6=OCH_2CH_3$, $M_1'=M_2'=M_3'=M_4'=M_5'=M_6'=H$
Compound C: $M_1=M_2=M_3=M_4=M_5=M_6=OCH_2CH_2CH_3$, $M_1'=M_2'=M_3'=M_4'=M_5'=M_6'=H$;
Compound D: $M_1=M_2=M_3=M_4=M_5=M_6=OCH(CH_3)_2$, $M_1'=M_2'=M_3'=M_4'=M_5'=M_6'=H$;
Compound E: $M_1=M_2=M_3=M_4=M_5=M_6=OCH_2CH_2CH_2CH_3$, $M_1'=M_2'=M_3'=M_4'=M_5'=M_6'=H$;
Compound F: $M_1=M_3=M_5=OCH_3$, $M_2=M_4=M_6=OCH_2CH_3$, $M_1'=M_2'=M_3'=M_4'=M_5'=M_6'=H$;
Compound G: $M_1=M_3=M_5=OCH_3$, $M_2=M_4=M_6=OCH_2CH_2CH_3$, $M_1'=M_2'=M_3'=M_4'=M_5'=M_6'=H$;
Compound H: $M_1=M_3=M_5=OCH_3$, $M_2=M_4=M_6=OCH_2CH_2CH_2CH_3$, $M_1'=M_2'=M_3'=M_4'=M_5'=M_6'=H$;
Compound I: $M_1=M_2=M_3=M_4=M_5=M_6=OH$, $M_1'=M_2'=M_3'=M_4'=M_5'=M_6'=H$;
Compound J: $M_1=M_3=M_5=OCH_3$, $M_2=M_4=M_6=OH$, $M_1'=M_2'=M_3'=M_4'=M_5'=M_6'=H$;
Compound K: $M_1=M_3=M_5=OCH_3$, $M_2=M_4=M_6=NH_2$, $M_1'=M_2'=M_3'=M_4'=M_5'=M_6'=H$;
Compound L: $M_1=M_3=M_5=OCH_3$, $M_2=M_4=M_6=Cl$, $M_1'=M_2'=M_3'=M_4'=M_5'=M_6'=H$;
Compound M: $M_1=M_3=M_5=OCH_3$, $M_2=M_4=M_6=Br$, $M_1'=M_2'=M_3'=M_4'=M_5'=M_6'=H$;
Compound N: $M_1=M_3=M_5=OCH_3$, $M_2=M_4=M_6=I$, $M_1'=M_2'=M_3'=M_4'=M_5'=M_6'=H$;
Compound O: $M_1=M_3=M_5=OCH_3$, $M_2=M_4=M_6=CHO$, $M_1'=M_2'=M_3'=M_4'=M_5'=M_6'=H$;
Compound P: $M_1=M_3=M_5=OCH_3$, $M_2=M_4=M_6=OCH_2CH_2Br$, $M_1'=M_2'=M_3'=M_4'=M_5'=M_6'=H$;
Compound Q: $M_1=M_2=M_3=M_4=M_5=M_6=OCH_2CH_2Cl$, $M_1'=M_2'=M_3'=M_4'=M_5'=M_6'=H$;
Compound R: $M_1=M_3=M_5=OH$, $M_2=M_4=M_6=OCH_2CH_3$, $M_1'=M_2'=M_3'=M_4'=M_5'=M_6'=H$;
Compound S: $M_1=M_2=M_3=M_4=M_5=M_6=OCH_3$, $M_1'=Cl$, $M_2'=M_3'=M_4'=M_5'=M_6'=H$;
Compound T: $M_1=M_2=M_3=M_4=M_5=M_6=OCH_3$, $M_1'=M_3'=Cl$, $M_2'=M_4'=M_5'=M_6'=H$;
Compound U: $M_1=M_2=M_3=M_4=M_5=M_6=OCH_3$, $M_1'=M_3'=M_5'=Cl$, $M_2'=M_4'=M_6'=H$;
Compound V: $M_1=M_2=M_3=M_4=M_5=M_6=OCH_3$, $M_1'=M_3'=M_6'=Cl$, $M_2'=M_4'=M_5'=H$;
Compound W: $M_1=M_2=M_3=M_4=M_5=M_6=OCH_2CH_3$, $M_1'=M_3'=M_5'=NO_2$, $M_2'=M_4'=M_6'=H$.

In addition, when $M_1=M_3=M_5=X$ and $M_2=M_4=M_6=Y$ (X and Y represent respectively an above-described selectable group for $M_1$, $M_3$ and $M_5$ and an above-described selectable group for $M_2$, $M_4$ and $M_6$, and X is different from Y), the cyclotriveratrylene and derivatives thereof represented by the formula (I) may have the following isomers: $M_1=M_4=M_5=X$, $M_2=M_3=M_6=Y$; $M_2=M_4=M_5=X$, $M_1=M_3=M_6=Y$; and/or $M_2=M_4=M_6=X$, $M_1=M_3=M_5=Y$. Such isomers are also within the scope of the present disclosure.

Likewise, when $M_1'=M_3'=M_5'=X$ and $M_2'=M_4'=M_6'=Y$ (X and Y represent respectively an above-described selectable group for $M_1'$, $M_3'$ and $M_5'$ and an above-described selectable group for $M_2'$, $M_4'$ and $M_6'$, and X is different from Y), the cyclotriveratrylene and derivatives thereof represented by the formula (I) may have the following isomers: $M_1'=M_4'=M_5'=X$, $M_2'=M_3'=M_6'=Y$; $M_2'=M_4'=M_5'=X$, $M_1'=M_3'=M_6'=Y$; and/or $M_2'=M_4'=M_6'=X$, $M_1'=M_3'=M_5'=Y$. Such isomers are also within the scope of the present disclosure.

The cyclotriveratrylene and derivatives thereof useful in the present disclosure may be prepared by processes known per se. For example, the cyclotriveratrylene and derivatives thereof may be prepared by one of the following processes:

Process I: in the presence of an acidic substance and an optional halogenated hydrocarbon, benzene derivative A represented by formula (IV) reacts with formaldehyde or a precursor thereof, to afford the cyclotriveratrylene and derivatives thereof;

Process II: in the presence of an acidic substance, benzene derivative B represented by formula (V) is catalytically condensed, to afford the cyclotriveratrylene and derivatives thereof; Process III: in the presence of a Lewis acid, benzene derivative A represented by formula (IV) reacts catalytically with formaldehyde or a precursor thereof in a halogenated hydrocarbon, to afford the cyclotriveratrylene and derivatives thereof;

Formula (IV)

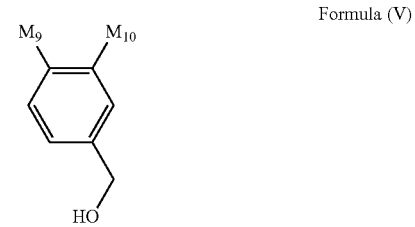

Formula (V)

wherein $M_7$, $M_8$, $M_9$ and $M_{10}$ are the same as defined above for $M_1$ to $M_6$ in the formula (I).

The acidic substance may be at least one selected from the group consisting of hydrochloric acid, perchloric acid, hydrobromic acid, hydroiodic acid, sulfuric acid, pyrosulfuric acid, sulfurous acid, phosphoric acid, pyrophosphoric acid, phosphorous acid, boric acid, formic acid, acetic acid, benzoic acid, trifluoroacetic acid, sulfonic acid and benzene sulfonic acid.

The halogenated hydrocarbon may be at least one selected from the group consisting of tetrachlorocarbon, chloroform, dichloromethane, bromomethane, chloroethane, chloropropane, chlorobutane, chloropentane, chlorohexane, bromoethane, 1,2-dichloroethane, 1,3-dichloropropane, 1,4-dichlorobutane, 1,5-dichloropentane, 1,6-dichlorohexane, chlorocyclopentane, chlorocyclohexane, chlorobenzene, dichlorobenzene and bromobenzene.

The Lewis acid may be at least one selected from the group consisting of boron trifluoride-diethyl ether, iron trichloride, aluminum trichloride and titanium tetrachloride.

The precursor of formaldehyde may be a paraformaldehyde, for example, triformol.

In the above processes, the amounts of the various raw materials used may be selected according to conventional techniques, and this is within the scope of knowledges of those skilled in the art.

According to the use of the present disclosure, the cyclotriveratrylene and derivatives thereof of the formula (I)

can be used as an internal electron donor compound in solid catalyst components (main catalyst) of Ziegler-Natta-type olefin polymerization catalysts, or as an external electron donor compound of Ziegler-Natta-type olefin polymerization catalysts, or the both.

In the present disclosure, there are not specific limitations to the Ziegler-Natta-type olefin polymerization catalysts, in which the cyclotriveratrylene and derivatives thereof of the formula (I) can be used, as well as the preparation thereof. The present inventors have found that the cyclotriveratrylene and derivatives thereof of the formula (I) may be introduced into various known Ziegler-Natta-type olefin polymerization catalysts as, for example, a replacement or a supplement of the internal electron donor or the external electron donor or the both comprised therein.

A first use of the first aspect of the present disclosure relates to use of the cyclotriveratrylene and derivatives thereof of the formula (I) as an internal electron donor compound in olefin polymerization catalyst systems, in which use the cyclotriveratrylene and derivatives thereof of the formula (I) are introduced, as an ingredient of solid catalyst component, into the solid catalyst component of the olefin polymerization catalyst systems.

According to the first use, there are not specific limitations to the solid catalyst component, into which the cyclotriveratrylene and derivatives thereof of the formula (I) are introduced, as well as the preparation thereof. The present inventors have found that the cyclotriveratrylene and derivatives thereof of the formula (I) may be introduced, as an internal electron donor component, into various solid catalyst components for olefin polymerization known in the art. The olefin polymerization catalysts comprising the so-obtained solid catalyst components can exhibit good copolymerization property and activity, but also can exhibit high polymerization activity and high polymer melt index under condition of high hydrogen gas-ethylene ratio (for example, hydrogen gas partial pressure/ethylene partial pressure ≥1.5).

In some embodiments of the first use, the olefin polymerization catalyst comprises a reaction product of:

1) a solid catalyst component comprising magnesium, titanium, halogen and an internal electron donor compound;

2) a cocatalyst, for example, an organic aluminum compound such as alkyl aluminum compound; and 3) an optional external electron donor component, wherein the internal electron donor compound comprises at least one of the above-described cyclotriveratrylene and derivatives thereof. In some embodiments, the solid catalyst component comprises a reaction product of a magnesium compound, a titanium compound and an internal electron donor compound.

The magnesium compound and the titanium compound are those commonly used in the preparation of Ziegler-Natta-type olefin polymerization catalysts.

In general, the magnesium compound may be at least one selected from the group consisting of magnesium halides, hydrates and alcohol-adducts of magnesium halides, alkyl magnesiums, and derivatives in which a halogen atom (at least one) in the formula of magnesium halides is replaced by an alkoxy or a halogenated alkoxy.

The titanium compound may be represented by the following general formula: $Ti(OR)_nX'_{4-n}$, where R is a $C_1$-$C_8$ hydrocarbyl, preferably a $C_1$-$C_8$ alkyl, X' is halogen, for example, fluorine, chlorine or bromine, and 0≤n≤4. Preferably, the titanium compound is at least one selected from the group consisting of titanium tetrachloride, titanium tetrabromide, tetraethoxy titanium, triethoxy titanium chloride, diethoxy titanium dichloride and ethoxy titanium trichloride. More Preferably, the titanium compound is titanium tetrachloride.

In a preferred embodiment, the solid catalyst component comprises the titanium compound and the cyclotriveratrylene and derivatives thereof, supported on the magnesium halide.

In other embodiments, the solid catalyst component comprises a reaction product of a finely-divided support, a magnesium halide, a titanium halide and an internal electron donating compound, wherein the finely-divided support has a particle size of from 0.01-10 microns, and the finely-divided support may be at least one selected from the group consisting of alumina, activated carbon, clays, silica, Mania, magnesia, zirconia, polystyrenes and calcium carbonate.

In some embodiments, a molar ratio of the cyclotriveratrylene and derivatives thereof to magnesium (or magnesium compound) in the solid catalyst component ranges from 0.0005:1 to 0.1:1, preferably from 0.001:1 to 0.1:1, and more preferably from 0.002:1 to 0.05:1.

In some embodiments, in the preparation of the catalyst component, a molar ratio of the titanium halide to the magnesium halide ranges from 1:20 to 1:2, a molar ratio of the titanium halide to the electron donor b ranges from 1:1 to 1:600, and a molar ratio of the titanium halide to the electron donor a ranges from 5:1 to 2000:1.

In some embodiments, in addition to the cyclotriveratrylene and derivatives thereof (referred to hereinafter as "internal electron donor a"), the internal electron donating compound may further comprise other internal electron donors commonly used in the art (referred to hereinafter as internal electron donor b) different from the internal electron donor a, for example, alcohols, organic acids, esters of organic acids, organic acyl halides, organic anhydrides, ethers, ketones, amines, phosphates, amides, carbonates, phenols, pyridine, macromolecule compounds carrying a polar group, and the like. For example, the internal electron donor b may be at least one selected from the group consisting of methyl acetate, ethyl acetate, propyl acetate, butyl acetate, n-octyl acetate, methyl benzoate, ethyl benzoate, butyl benzoate, hexyl benzoate, ethyl p-methylbenzoate, methyl naphthalene carboxylate, ethyl naphthalene carboxylate, methyl methacrylate, ethyl acrylate, butyl acrylate, diethyl ether, dibutyl ether, tetrahydrofuran, 2,2-dimethyl-1,3-diethoxypropane, methanol, ethanol, propanol, isopropanol, butanol, isooctanol, octyl amine, triethylamine, acetone, butanone, cyclopentanone, 2-methylcyclopentanone, cyclohexanone, phenol, hydroquinone, organic epoxy compounds (for example, epoxy ethane, epoxy propane, epoxy chloropropane, polyepichlorohydrin, polyoxyethylene), organophosphorus compounds (for example, trimethyl phosphate, triethyl phosphate, tripropyl phosphate, tributyl phosphate, triphenyl phosphate, trihexyl phosphate), polymethyl methacrylates and polystyrenes.

According to the first use, when the internal electron donor b is included, a molar ratio of the internal electron donor b to titanium in the solid catalyst component may range from 1000:1 to 1:1000.

A second use of the first aspect of the present disclosure relates to use of the cyclotriveratrylene and derivatives thereof of the formula (I) as an external electron donor compound in olefin polymerization catalyst systems, in which use the cyclotriveratrylene and derivatives thereof of the formula (I) are introduced, together with a solid catalyst component and a cocatalyst, into a polymerization reactor, with or without a pre-contact between the solid catalyst component, the cocatalyst and the compound of the formula (I).

According to the second use, there are not specific limitations to the solid catalyst component, with which the cyclotriveratrylene and derivatives thereof of the formula (I) are used together, as well as the preparation thereof. For example, the solid catalyst component may be the solid catalyst component according to the present disclosure or any Ziegler-Natta-type solid catalyst component known in the art to be useful in olefin polymerization. The present inventors have found that, when the above-described cyclotriveratrylene and derivatives thereof are used as an external electron donor, the olefin polymerization catalyst systems exhibit good copolymerization property.

In some embodiments of the second use, the olefin polymerization catalyst comprises a reaction product of:

1) a solid catalyst component comprising magnesium, titanium, halogen and an optional internal electron donor compound;

2) a cocatalyst, for example, an organic aluminum compound such as alkyl aluminum compound; and 3) an external electron donor compound;

wherein the external electron donor compound comprises at least one of the above-described cyclotriveratrylene and derivatives thereof.

In some embodiments, the solid catalyst component is a reaction product of a magnesium compound, a titanium compound and an optional internal electron donor compound.

The magnesium compound and the titanium compound are as described above.

According to the second use, a molar ratio of the external electron donor or the cyclotriveratrylene and derivatives thereof to titanium in the solid catalyst component ranges from 0.05:1 to 50:1.

The optional internal electron donor compound may be any compound known in the art to be useful as an internal electron donor in a solid catalyst component for olefin polymerization. For example, the optional internal electron donor compound may be selected from those as described for the internal electron donor b in the first use. In addition, the internal electron donor compound also optionally comprises the cyclotriveratrylene and derivatives thereof (i.e., internal electron donor a). When the internal electron donating compound comprises the cyclotriveratrylene and derivatives thereof, the solid catalyst component is just the solid catalyst component mentioned in the first use as described above.

In some embodiments, the cocatalyst may be any organic aluminum compound known in the art to be useful as a cocatalyst of olefin polymerization catalysts. For example, the organic aluminum compound is of general formula $AlR'_d X'_{3-d}$ where R' is hydrogen or a $C_1$-$C_{20}$ hydrocarbyl, X' is a halogen atom, and $0<d\leq3$. The $C_1$-$C_{20}$ hydrocarbyl is, for example, $C_1$-$C_{20}$ alkyl, aralkyl or aryl. The organic aluminum compound is preferably selected from the group consisting of $Al(CH_3)_3$, $Al(CH_2CH_3)_3$, $Al(i-Bu)_3$, $AlH(CH_2CH_3)_2$, $Al[(CH_2)_5CH_3]_3$, $AlH(i-Bu)_2$, $AlCl(CH_2CH_3)_2$, $Al_2Cl_3(CH_2CH_3)_3$, $AlCl(CH_2CH_3)_2$, $AlCl(CH_2CH_3)$, and more preferably from the group consisting of $Al(CH_2CH_3)_3$, $Al[(CH_2)_5CH_3]_3$ and/or $Al(i-Bu)_3$.

In some embodiments, in the catalyst, a molar ratio of aluminum in the component 2) to titanium in the component 1) may range from 5:1 to 500:1, and preferably from 20:1 to 200:1.

More details about the catalysts for olefin polymerization and the solid catalyst components therein will be given hereinbelow.

In a second aspect, the present disclosure provides an olefin polymerization catalyst system, comprising at least one of the above-described cyclotriveratrylene and derivatives thereof represented by the formula (I) or (I') as (i) an internal electron donor, (ii) an external electron donor, or (iii) the both.

In a subaspect of this aspect, the present disclosure provides a solid catalyst component for olefin polymerization, comprising at least one of the above-described cyclotriveratrylene and derivatives thereof represented by the formula (I) or (I') as an internal electron donor compound.

In the present disclosure, there are not specific limitations to the solid catalyst component for olefin polymerization as well as the preparation thereof, as long as the solid catalyst component comprises at least one of the above-described cyclotriveratrylene and derivatives thereof represented by the formula (I) or (I') as an internal electron donor compound. For example, the solid catalyst component may be any solid catalyst component for olefin polymerization known in the art, only with a proviso that it comprises at least one of the above-described cyclotriveratrylene and derivatives thereof represented by the formula (I) or formula (I') as, for example, a replacement or a supplement of the internal electron donor comprised therein.

In some embodiments, the solid catalyst component comprises magnesium, titanium, halogen and an internal electron donor compound, wherein the internal electron donor compound comprises at least one compound represented by the above-described formula (I) or (I').

As for this solid catalyst component, in some preferred embodiments, the solid catalyst component comprises a titanium compound and the cyclotriveratrylene and derivatives thereof, supported on a magnesium halide. Preferably, a molar ratio of the cyclotriveratrylene and derivatives thereof to the magnesium halide ranges from 0.0005:1 to 0.1:1, preferably from 0.001:1 to 0.1:1, and more preferably from 0.002:1 to 0.05:1. Preferably, the titanium compound is of general formula $Ti(OR)_n X'_{4-n}$, where R is a $C_1$-$C_8$ hydrocarbyl, X' is a halogen atom, and $0\leq n\leq 4$; and more preferably, the titanium compound is at least one selected from the group consisting of titanium tetrachloride, titanium tetrabromide, tetraethoxy titanium, triethoxy titanium chloride, diethoxy titanium dichloride, tetrabutoxy titanium and ethoxy titanium trichloride.

In some embodiments, the solid catalyst component comprises a reaction product of: a magnesium halide-alcohol adduct, a titanium compound, an internal electron donor compound, and an optional organic aluminum compound, wherein the internal electron donor compound comprises at least one compound represented by the above-described formula (I).

As for this solid catalyst component, in some preferred embodiments, the magnesium halide-alcohol adduct is of general formula $MgX_2 \cdot m(ROH)$, where X is Cl, Br or I, preferably Cl; R is a $C_1$-$C_6$ alkyl; and m is from 0.5 to 4.0, and preferably from 2.5 to 4.0.

As for this solid catalyst component, in some preferred embodiments, the titanium compound is of general formula $Ti(OR^2)_n X^2_{4-n}$, where $R^2$ is a $C_1$-$C_8$ hydrocarbyl, preferably a $C_1$-$C_8$ alkyl; $X^2$ is Cl, Br or I; and $0\leq n\leq 4$; and preferably, the titanium compound is at least one selected from the group consisting of $TiCl_4$, $Ti(OC_2H_5)Cl_3$, $Ti(OCH_3)Cl_3$, $Ti(OC_4H_9)Cl_3$, and $Ti(OC_4H_9)_4$.

As for this solid catalyst component, in some preferred embodiments, the organic aluminum compound is of general formula $AlR^1_aX^1_bH_c$, where $R^1$ is a $C_1$-$C_{14}$ hydrocarbyl, $X^1$ is a halogen atom, and a preferably fluorine, chlorine, bromine, each a, b and c is a number of from 0 to 3, and a+b+c=3.

As for this solid catalyst component, in some preferred embodiments, the content of the at least one compound represented by formula (I) is at least 0.0005 moles, preferably at least 0.001 moles, and preferably from 0.001 to 0.1 moles, relative to one mole of magnesium.

As for this solid catalyst component, in some preferred embodiments, in a reaction for forming the solid catalyst component, relative to one mole of magnesium, the amount of the titanium compound used ranges from 0.1 to 100 moles, and preferably from 1 to 50 moles; the amount of the organic aluminum compound used ranges from 0 to 5 moles; and the amount of the cyclotriveratrylene compound is at least 0.0005 moles, preferably at least 0.001 moles, and preferably from 0.001 to 0.1 moles.

In some embodiments, the solid catalyst component comprises a reaction product of: an alkoxy magnesium compound, a titanium compound and an internal electron donor compound, wherein the internal electron donor compound comprises at least one compound represented by the above-described formula (I).

As for this solid catalyst component, in some preferred embodiments, the alkoxy magnesium compound is of general formula $Mg(OR_3)_a(OR_4)_{2-a}$, where $R_3$ and $R_4$ are identical or different, and are each selected from the group consisting of substituted or unsubstituted $C_1$-$C_{10}$ hydrocarbyl groups, the substituent being selected from the group consisting of hydroxy, amino, aldehyde group, carboxy, acyl, halogen atoms, alkoxy and heteroatom, and $0 \leq a \leq 2$.

As for this solid catalyst component, in some preferred embodiments, the titanium compound is of general formula $Ti(OR)_nX_{4-n}$, where R is a $C_1$-$C_8$ hydrocarbyl, preferably a $C_1$-$C_8$ alkyl; X is a halogen atom; and $0 \leq n \leq 4$; and preferably the titanium compound is at least one selected from the group consisting of $TiCl_4$, $Ti(OC_2H_5)Cl_3$, $Ti(OCH_3)Cl_3$, $Ti(OC_4H_9)Cl_3$ and $Ti(OC_4H_9)_4$.

As for this solid catalyst component, in some preferred embodiments, the content of the at least one compound represented by the formula (I) is at least 0.0005 moles, preferably at least 0.001 moles, and preferably from 0.001 to 0.1 moles, relative to one mole of magnesium.

As for this solid catalyst component, in some preferred embodiments, in a reaction for forming the solid catalyst component, relative to one mole of magnesium, the amount of the titanium compound used ranges from 0.1 to 100 moles, and preferably from 1 to 50 moles; and the amount of the cyclotriveratrylene compound used is at least 0.0005 moles, preferably at least 0.001 moles, and preferably from 0.001 to 0.1 moles.

In some embodiments, the solid catalyst component comprises a reaction product of: a finely-divided support having a particle size of from 0.01 to 10 microns; a magnesium halide; a titanium halide; and an internal electron donating compound, wherein the internal electron donating compound comprises an internal electron donor a and an internal electron donor b, wherein the internal electron donor a is at least one compound represented by the above-described formula (I), and the internal electron donor b is at least one selected from the group consisting of alkyl esters of $C_2$-$C_{10}$ saturated aliphatic carboxylic acids, alkyl esters of $C_7$-$C_{10}$ aromatic carboxylic acids, $C_2$-$C_{10}$ aliphatic ethers, $C_3$-$C_{10}$ cyclic ethers, and $C_3$-$C_{10}$ saturated aliphatic ketones.

As for this solid catalyst component, in some preferred embodiments, the magnesium halide is at least one selected from the group consisting of $MgCl_2$, $MgBr_2$ and $MgI_2$.

As for this solid catalyst component, in some preferred embodiments, the titanium halide is titanium tetrachloride and/or titanium trichloride.

As for this solid catalyst component, in some preferred embodiments, the finely-divided support is at least one selected from the group consisting of alumina, activated carbon, clays, silica, titania, polystyrenes and calcium carbonate.

As for this solid catalyst component, in some preferred embodiments, a molar ratio of the titanium halide to the internal electron donor a ranges from 5:1 to 2000:1, and a molar ratio of the titanium halide to the internal electron donor b ranges from 1:1 to 1:600.

As for this solid catalyst component, in some preferred embodiments, the internal electron donor b is at least one selected from the group consisting of methyl formate, ethyl acetate, butyl acetate, diethyl ether, dihexyl ether, tetrahydrofuran, acetone and methyl isobutyl ketone.

In some embodiments, the solid catalyst component comprises a reaction product of:

1) a magnesium-containing liquid-state component, which is at least one selected from the following components:

i) an alkyl magnesium or a solution thereof in a liquid hydrocarbon, the alkyl magnesium being of general formula $MgR_1R_2$, where $R_1$ and $R_2$ are each independently selected from the group consisting of $C_1$-$C_{10}$ hydrocarbyl groups, which are unsubstituted or substituted by a substituent selected from the group consisting of hydroxy, amino, aldehyde group, carboxy, halogen atoms, alkoxy and heteroatoms;

ii) a product obtained by dissolving, in a solvent system comprising an organophosphorus compound, an organic epoxy compound and an optional alcohol compound $R_5OH$, a magnesium dihalide or a derivative deriving from a magnesium dihalide by replacing one halogen atom in the molecular formula of the magnesium dihalide with group $R_3$ or $OR_4$; and iii) a product obtained by dispersing a magnesium dihalide or a derivative deriving from a magnesium dihalide by replacing one halogen atom in the molecular formula of the magnesium dihalide with group $R_3$ or $OR_4$ in an alcohol compound $R_5OH$;

wherein $R_3$, $R_4$ and $R_5$ are each independently selected from the group consisting of $C_1$-$C_{10}$ hydrocarbyl groups, which are unsubstituted or substituted by a substituent selected from the group consisting of hydroxy, amino, aldehyde group, carboxy, halogen atoms, alkoxy and heteroatoms;

2) a titanium compound;

3) an internal electron donor compound, which comprises at least one compound represented by the above-described formula (I); and 4) optionally, an auxiliary precipitant, which is selected from the group consisting of organic anhydride compounds and/or organic silicon compounds.

As for this solid catalyst component, in some preferred embodiments, the alkyl magnesium is at least one selected from the group consisting of dimethyl magnesium, diethyl magnesium, n-butyl ethyl magnesium, di-n-butyl magnesium, and butyl octyl magnesium.

As for this solid catalyst component, in some preferred embodiments, the magnesium dihalide or derivative deriving from a magnesium dihalide by replacing one halogen atom in the molecular formula of the magnesium dihalide with group $R_3$ or $OR_4$ is at least one selected from the group consisting of $MgCl_2$, $MgBr_2$, $MgI_2$, $MgCl(OCH_2CH_3)$, $MgCl(OBu)$, $CH_3MgCl$ and $CH_3CH_2MgCl$.

As for this solid catalyst component, in some preferred embodiments, the organophosphorus compound is selected from the group consisting of hydrocarbyl esters and halogenated hydrocarbyl esters of ortho-phosphoric acid, and hydrocarbyl esters and halogenated hydrocarbyl esters of phosphorous acid, preferably at least one selected from the group consisting of triethyl phosphate, tributyl phosphate, tri-isooctyl phosphate, triphenyl phosphate, triethyl phosphite, tributyl phosphite and di-n-butyl phosphite.

As for this solid catalyst component, in some preferred embodiments, the organic epoxy compound is at least one selected from the group consisting of aliphatic epoxy compounds and diepoxy compounds, halogenated aliphatic epoxy compounds and diepoxy compounds, glycidyl ethers, and inner ethers, having from 2 to 18 carbon atoms, preferably at least one selected from the group consisting of epoxy ethane, epoxy propane, epoxy butane, vinyl epoxy ethane, epoxy chloropropane, glycidyl methacrylate, glycidyl ethyl ether and glycidyl butyl ether.

As for this solid catalyst component, in some preferred embodiments, the alcohol compound is at least one selected from the group consisting of methanol, ethanol, propanol, isopropanol, butanol, isobutanol, tert-butanol, hexanol, cyclohexanol, octanol, isooctanol, decanol, benzyl alcohol and phenylethanol.

As for this solid catalyst component, in some preferred embodiments, the titanium compound is of general formula $Ti(OR_6)_nX_{4-n}$, where $R_6$ is a $C_1$-$C_8$ hydrocarbyl, X is a halogen atom, and $0 \leq n \leq 3$; and the titanium compound is preferably at least one selected from the group consisting of $TiCl_4$, $TiBr_4$, $Ti(OC_2H_5)Cl_3$, $Ti(OCH_3)Cl_3$, $Ti(OC_4H_9)Cl_3$, $Ti(OC_2H_5)Br_3$, $Ti(OC_2H_5)_2Cl_2$, $Ti(OCH_3)_2Cl_2$, $Ti(OCH_3)_2I_2$, $Ti(OC_2H_5)_3Cl$, $Ti(OCH_3)_3Cl$ and $Ti(OC_2H_5)_3I$.

As for this solid catalyst component, in some preferred embodiments, the organic anhydride compounds are represented by formula (II): $R^1CO-O-CO-R^2$ (II), where $R^1$ and $R^2$ are each independently selected from the group consisting of hydrogen and $C_1$-$C_{10}$ hydrocarbyl groups, and the $R^1$ and $R^2$ may optionally be linked to form a ring.

As for this solid catalyst component, in some preferred embodiments, the organic silicon compounds are of general formula $R^3_xR^4_ySi(OR^5)_z$, where $R^3$ and $R^4$ are each independently selected from the group consisting of $C_1$-$C_{10}$ hydrocarbyl groups and halogen atoms; $R^5$ is a $C_1$-$C_{10}$ hydrocarbyl; each x, y and z is an positive integer, $0 \leq x \leq 2$, $0 \leq y \leq 2$, $0 \leq z \leq 4$, and $x+y+z=4$.

As for this solid catalyst component, in some preferred embodiments, in a reaction for forming the solid catalyst component, relative to one mole of magnesium, the amount of the titanium compound used ranges from 0.5 to 120 moles, preferably from 1 to 50 moles; and the amount of the cyclotriveratrylene and derivatives thereof used ranges from 0.0005 to 1 mole, preferably from 0.001 to 1 mole, and preferably from 0.001 to 0.05 moles.

As mentioned above, there are not specific limitations to the process for the preparation of the solid catalyst component of the disclosure. In principle, it is possible to prepare the solid catalyst component of the disclosure by using any process for the preparation of a solid catalyst component known in the art, with a proviso that the cyclotriveratrylene and derivatives thereof of the formula (I) is introduced, as an internal electron donor, before, during or after the formation of the solid catalyst component.

In some embodiments, the solid catalyst component may be prepared by a process comprising the following steps:

(1) preparing a mother liquor: a magnesium halide, a titanium halide, and an internal electron donor compound are mixed and allowed to react at 0 to 90° C. for 0.5 to 5 hours, to afford the mother liquor;

(2) preparing a finely-divided support-admixed mother liquor: at 0 to 90° C., the mother liquor from step (1) and a finely-divided support are mixed and stirred for 0.5 to 3 hours, to afford the finely-divided support-admixed mother liquor;

(3) spray forming: the finely-divided support-admixed mother liquor is spray-dried, to obtain the solid catalyst component, wherein the content of the finely-divided support in the finely-divided support-admixed mother liquor ranges from 3 to 50 wt. %, and preferably from 10 to 30 wt. %.

In other embodiments, the solid catalyst component may be prepared by a process comprising the following steps:

1) dissolving a magnesium halide in a solvent system comprising an organic epoxy compound, an organophosphorus compound, an organic alcohol and an internal electron donor a to form a homogenous solution;

2) contacting and reacting the above solution with a titanium compound and an organic siloxane at a low temperature, with solid particles comprising magnesium, titanium, a halogen and an alkoxy group then gradually precipitating in course of gradually raising the temperature;

3) removing the liquid from the reaction mixture, and washing the residual solids (for example, with an inert solvent) to afford the solid catalyst component.

In other embodiments, the solid catalyst component may be prepared by a process comprising the following steps:

1) contacting and reacting a magnesium halide with an alcohol compound and an internal electron donor compound in the presence of an inert solvent;

2) adding an organic silicon compound thereto and allowing them to contact and react;

3) contacting and reacting the system from step 2) with a titanium compound; and 4) removing the liquid from the reaction mixture and washing the residual solids, to afford the solid catalyst component.

In other embodiments, the solid catalyst component may be prepared by a process comprising the following steps:

1) dispersing a magnesium halide-alcohol adduct in an inert solvent to afford a suspension;

2) contacting and reacting the suspension with an organic aluminum compound and an internal electron donor compound, then removing the liquid from the reaction mixture, and washing the residual solids;

3) contacting and reacting the solids from step 2) with a titanium compound in the presence of an inert solvent, then removing the liquid from the reaction mixture, and washing the residual solids to afford the solid catalyst component.

More details about this process can be found in CN102807638A, the whole disclosure of which is incorporated herein by reference.

In other embodiments, the solid catalyst component may be prepared by a process comprising the following steps:

1) dispersing an alkoxy magnesium compound in an inert solvent to afford a suspension;

2) contacting and reacting the suspension with a titanium compound, then removing the liquid from the reaction mixture, and washing the residual solids;

3) contacting and reacting the precipitants from step 2) with a titanium compound and an internal electron donor compound in the presence of an inert solvent, then removing the liquid from the reaction mixture, and washing the residual solids to afford the solid catalyst component.

The above-described processes are known per se, except that the cyclotriveratrylene and derivatives thereof are additionally or alternatively used as an internal electron donor/an internal electron donor a. The other reactants involved in these processes are as described above. In general, the cyclotriveratrylene and derivatives thereof may be incorporated into the solid catalyst component before, during or after the formation of particles of the solid catalyst component, and preferably before or during the formation of particles of the solid catalyst component.

In some specific embodiments, the solid catalyst component may be prepared by a process comprising the following steps:

1) dispersing an alkoxy magnesium compound in an inert solvent to afford a suspension;

2) contacting and reacting the suspension with a titanium compound and the cyclotriveratrylene and derivatives thereof, then removing the liquid from the reaction mixture, and washing the residual solids;

3) contacting and reacting the mixture from step 2) with a titanium compound, optionally in the presence of an inert solvent, then removing the liquid from the reaction mixture, and washing the residual solids to afford the solid catalyst component.

In other specific embodiments, the solid catalyst component may be prepared by a process comprising the following steps:

1) dispersing an alkoxy magnesium compound in an inert solvent to afford a suspension;

2) contacting and reacting the suspension with a titanium compound, then removing the liquid from the reaction mixture, and washing the residual solids;

3) contacting and reacting the mixture from step 2) with a titanium compound and the cyclotriveratrylene and derivatives thereof, optionally in the presence of an inert solvent, then removing the liquid from the reaction mixture, and washing the residual solids to afford the solid catalyst component.

In other specific embodiments, the solid catalyst component may be prepared by a process comprising the following steps:

(1) preparing a mother liquor: a magnesium halide, a titanium halide, an internal electron donor a and an internal electron donor b are mixed and allowed to react at 0 to 90° C. for 0.5 to 5 hours to afford the mother liquor;

(2) preparing a finely-divided support-admixed mother liquor: the mother liquor from step (1) and a finely-divided support are mixed and stirred at 0 to 90° C. for 0.5 to 3 hours to afford the finely-divided support-admixed mother liquor, wherein the content of the finely-divided support in the finely-divided support-admixed mother liquor ranges preferably from 3 to 50 wt. %, and more preferably from 10 to 30 wt. %; and (3) spray forming: the finely-divided support-admixed mother liquor is spray-dried, to afford the solid catalyst component.

In another subaspect of the second aspect of the present disclosure, the present disclosure provides an olefin polymerization catalyst, comprising a reaction product of:

1) the above-described solid catalyst component of the disclosure;

2) a cocatalyst, for example, an organic aluminum compound such as alkyl aluminum compound; and 3) an optional external electron donor component.

As for this subaspect, in some embodiments, the optional external electron donor component may comprise any of compounds known in the art to be useful as an external electron donor in an olefin polymerization catalyst system, for example, organic silanes, and/or comprise at least one of the above-described cyclotriveratrylene and derivatives thereof.

In this subaspect, there are not strict limitations to the cocatalyst, and any of those known in the art to be useful as a cocatalyst of olefin polymerization catalyst systems can be used. In some embodiments, the cocatalyst is an organic aluminum compound of general formula $AlR^3{}_aX^3{}_bH_c$, where $R^3$ is a $C_1$-$C_{20}$ hydrocarbyl; $X^3$ is a halogen atom, preferably Cl, Br or I; each a, b and c is a number of from 0 to 3, and a+b+c=3. Examples of the organic aluminum compound include $Al(CH_3)_3$, $Al(CH_2CH_3)_3$, $Al(i\text{-}Bu)_3$, $Al[(CH_2)_5CH_3]_3$, $AlH(CH_2CH_3)_2$, $AlCl(CH_2CH_3)_2$, $AlH(i\text{-}Bu)_2$, $AlCl_{1.5}(CH_2CH_3)_{1.5}$, $AlCl(CH_2CH_3)_2$ and $AlCl_2(CH_2CH_3)$. Preferably, the cocatalyst is a trialkyl aluminum, for example, trimethyl aluminum, triethyl aluminum, tri-isobutyl aluminum, tri-n-hexyl aluminum, tri-n-octyl aluminum, or the like.

In some preferred embodiments, a molar ratio of aluminum in the organic aluminum compound to titanium in the solid catalyst component ranges from 5:1 to 500:1, and preferably from 20:1 to 200:1.

In another subaspect of the second aspect of the present disclosure, the present disclosure provides an olefin polymerization catalyst, comprising a reaction product of:

1) a solid catalyst component comprising magnesium, titanium, a halogen and an optional internal electron donor compound;

2) a cocatalyst, for example, an organic aluminum compound; and 3) an external electron donor compound;

wherein the external electron donor compound comprises at least one of the above-described cyclotriveratrylene and derivatives thereof.

According to this subaspect, the solid catalyst component comprising magnesium, titanium, a halogen and an optional internal electron donor compound may be any of Ziegler-Natta-type solid catalyst components for olefin polymerization known in the art.

In some embodiments, the solid catalyst component comprises a titanium compound having at least one Ti-halogen bond, supported on a magnesium halide. Preferably, the titanium compound is selected from the group consisting of titanium trihalides and compounds of general formula $Ti(OR^2)_nX^2{}_{4-n}$, where $R^2$ is a $C_1$-$C_8$ hydrocarbyl, preferably a $C_1$-$C_8$ alkyl; $X^2$ is Cl, Br or I; and $0 \leq n \leq 4$; preferably, the titanium compound is at least one selected from the group consisting of $TiCl_3$, $TiCl_4$, $TiBr_4$, $Ti(OC_2H_5)Cl_3$, $Ti(OC_2H_5)_2Cl_2$ and $Ti(OC_2H_5)_3Cl$.

The cocatalyst is as described above.

In addition to the cyclotriveratrylene and derivatives thereof, the external electron donor component may further comprise any of compounds known in the art to be useful as an external electron donor of olefin polymerization catalyst systems, for example, an organic silane. This is within the scope of the present disclosure.

As for this solid catalyst component, the content of the optional internal electron donor compound ranges from 0 to 1 mole, relative to one mole of magnesium.

As for this subaspect, a molar ratio of aluminum in the cocatalyst such as organic aluminum compound to titanium in the solid catalyst component ranges from 5:1 to 500:1, and preferably from 20:1 to 200:1.

As for this subaspect, a molar ratio of the external electron donor compound to titanium in the solid catalyst component ranges from 0.05:1 to 50:1.

According to this subaspect, in some embodiments, the catalyst system comprises a reaction product of:

1) a solid catalyst component comprising a reaction product of: a magnesium halide-alcohol adduct, a titanium compound, an optional internal electron donor compound and an optional second organic aluminum compound, which is of general formula $AlR^3{}_aX^3{}_bH_c$, where $R^3$ is a $C_1$-$C_{14}$ hydrocarbyl; $X^3$ is a halogen atom, preferably Cl, Br or I; each a, b and c is a number of from 0 to 3, and a+b+c=3;

2) a cocatalyst, which is a first organic aluminum compound of general formula $AlR^1{}_dX^1{}_{3-d}$, where $R^1$ is hydrogen or a $C_1$-$C_{20}$ hydrocarbyl, $X^1$ is a halogen atom, and $0<d\leq3$;

3) an external electron donor compound comprising at least one of the above-described cyclotriveratrylene and derivatives thereof.

Preferably, the magnesium halide-alcohol adduct is of general formula $MgX_2 \cdot m(ROH)$, where X is Cl, Br or I, preferably Cl; R is a $C_1$-$C_6$ alkyl, preferably a $C_1$-$C_4$ alkyl; and m is from 0.5 to 4.0, and preferably from 2.5 to 4.0.

Preferably, the titanium compound is of general formula $Ti(OR^2)_nX^2{}_{4-n}$, where $R^2$ is a $C_1$-$C_8$ hydrocarbyl, preferably a $C_1$-$C_8$ alkyl; $X^2$ is Cl, Br or I; and $0\leq n\leq 4$; preferably, the titanium compound is at least one selected from the group consisting of $TiCl_4$, $Ti(OC_2H_5)Cl_3$, $Ti(OCH_3)Cl_3$, $Ti(OC_4H_9)Cl_3$ and $Ti(OC_4H_9)_4$.

Preferably, the second organic aluminum compound is at least one selected from the group consisting of $Al(CH_2CH_3)_3$, $Al(i-Bu)_3$ and $Al(n-C_6H_{13})_3$.

Preferably, in a reaction for forming the solid catalyst component, relative to one mole of magnesium, the amount of the titanium compound used ranges from 1 to 50 moles; the amount of the internal electron donor compound used ranges from 0 to 1 mole; and the amount of the second organic aluminum compound used ranges from 0 to 100 moles.

Preferably, a molar ratio of aluminum in the first organic aluminum compound to titanium in the solid catalyst component ranges from 5:1 to 500:1, and preferably from 20:1 to 200:1.

Preferably, a molar ratio of the external electron donor compound to titanium in the solid catalyst component ranges from 0.05:1 to 50:1.

According to this subaspect, in some embodiments, the present disclosure provides an olefin polymerization catalyst comprising a reaction product of:

1) a solid catalyst component comprising a reaction product of: an alkoxy magnesium compound, a titanium compound and an optional internal electron donor compound;

2) a cocatalyst;

3) an external electron donor compound comprising at least one of the above-described cyclotriveratrylene and derivatives thereof.

Preferably, the alkoxy magnesium compound is of general formula $Mg(OR_3)_a(OR_4)_2$, where $R_3$ and $R_4$ are each independently a substituted or unsubstituted $C_1$-$C_{10}$ alkyl, with substituent being hydroxy, amino, aldehyde group, carboxy, acyl, a halogen atom, alkoxy or a heteroatom, and $0\leq a\leq 2$.

Preferably, the titanium compound is of general formula $Ti(OR^2)_nX^2{}_{4-n}$, where $R^2$ is a $C_1$-$C_8$ hydrocarbyl, preferably a $C_1$-$C_8$ alkyl; $X^2$ is Cl, Br or I; and $0\leq n\leq 4$; preferably, the titanium compound is at least one selected from the group consisting of $TiCl_4$, $Ti(OC_2H_5)Cl_3$, $Ti(OCH_3)Cl_3$, $Ti(OC_4H_9)Cl_3$ and $Ti(OC_4H_9)_4$.

Preferably, in a reaction for forming the solid catalyst component, relative to one mole of magnesium, the amount of the titanium compound used ranges from 0.1 to 15 moles; and the amount of the internal electron donor compound used ranges from 0 to 0.1 moles.

The cocatalyst is as described above.

Preferably, a molar ratio of aluminum in the organic aluminum compound to titanium in the solid catalyst component ranges from 5:1 to 500:1, and preferably from 20:1 to 200:1.

Preferably, a molar ratio of the external electron donor compound to titanium in the solid catalyst component ranges from 0.05:1 to 50:1.

According to this subaspect, in some embodiments, the present disclosure provides an olefin polymerization catalyst comprising a reaction product of:

1) a solid catalyst component comprising a reaction product of: a finely-divided support, a magnesium halide, a titanium halide, an internal electron donor b and an optional internal electron donor a;

wherein the internal electron donor b is at least one selected from the group consisting of alkyl esters of $C_2$-$C_{10}$ saturated aliphatic carboxylic acids, alkyl esters of $C_7$-$C_{10}$ aromatic carboxylic acids, $C_2$-$C_{10}$ aliphatic ethers, $C_3$-$C_{10}$ cyclic ethers and $C_3$-$C_{10}$ saturated aliphatic ketones; and wherein the optional internal electron donor a is at least one selected from the group consisting of the cyclotriveratrylene and derivatives thereof represented by the formula (I);

2) a cocatalyst; and 3) an external electron donor compound comprising at least one of the above-described cyclotriveratrylene and derivatives thereof.

Preferably, the finely-divided support is at least one selected from the group consisting of alumina, activated carbon, clays, silica, titania, magnesia, zirconia, polystyrenes and calcium carbonate; and the finely-divided support has a particle size of from 0.01 to 10 μm.

Preferably, the magnesium halide is at least one selected from the group consisting of $MgCl_2$, $MgBr_2$ and $MgI_2$.

Preferably, the titanium halide is $TiCl_3$ and/or $TiCl_4$.

Preferably, in the solid catalyst component, a molar ratio of the titanium halide to the magnesium halide ranges from 1:20 to 1:2, and a molar ratio of the titanium halide to the internal electron donor b ranges from 1:1 to 1:600.

Preferably, a molar ratio of the external electron donor compound to titanium in the solid catalyst component ranges from 0.05:1 to 50:1.

According to this subaspect, in some embodiments, the present disclosure provides an olefin polymerization catalyst comprising a reaction product of:

1) a solid catalyst component comprising a reaction product of: a magnesium-containing liquid-state component, a titanium compound, an optional internal electron donor compound and an optional auxiliary precipitant, wherein the auxiliary precipitant is selected from the group consisting of organic anhydride compounds and/or organic silicon compound;

2) a cocatalyst; and 3) an external electron donor compound comprising at least one of the above-described cyclotriveratrylene and derivatives thereof.

Preferably, the magnesium-containing liquid-state component is at least one selected from the group consisting of the followings:

Component A: an alkyl magnesium compound of general formula $MgR_3R_4$;

Component B: a reaction product of a magnesium compound, an organophosphorus compound, an organic epoxy compound and an optional alcohol compound, the alcohol compound being of general formula $R_7OH$;

Component C: a reaction product of a magnesium compound and an alcohol compound, the alcohol compound being of general formula $R_7OH$, wherein the magnesium compound is of general formula $MgX^3{}_m R^3{}_{2-m}$, where $X^3$ is halogen, $R^3$ is $-R_5$ or $-OR_6$, m=1 or 2; $R_3$, $R_4$, $R_5$, $R_6$ and $R_7$ are identical or different, and are each a $C_1$-$C_{10}$ hydrocarbyl, which is unsubstituted or substituted by a substituent selected from the group consisting of hydroxy, amino, aldehyde group, carboxy, halogen atoms, alkoxy and heteroatoms.

Preferably, the titanium compound is of general formula $Ti(OR^2)_n X^2{}_{4-n}$, where $R^2$ is a $C_1$-$C_8$ hydrocarbyl, preferably a $C_1$-$C_8$ alkyl; $X^2$ is Cl, Br or I; and $0 \leq n \leq 4$; preferably, the titanium compound is at least one selected from the group consisting of $TiCl_4$, $Ti(OC_2H_5)Cl_3$, $Ti(OCH_3)Cl_3$ and $Ti(OC_4H_9)Cl_3$.

Preferably, the organic anhydride compound is at least one selected from those represented by formula (II): $R^1CO-O-CO-R2$ (II), where $R^4$ and $R^5$ are each independently selected from the group consisting of hydrogen, $C_1$-$C_{10}$ alkyl, $C_2$-$C_{10}$ alkenyl, $C_2$-$C_{10}$ alkynyl, $C_3$-$C_8$ cycloalkyl and $C_6$-$C_{10}$ aromatic hydrocarbyl, and $R^4$ and $R^5$ may optionally be linked to form a ring.

Preferably, the organic silicon compound is of general formula $R^6{}_x R^7{}_y Si(OR^8)_z$, where $R^6$ and $R^7$ are each independently a $C_1$-$C_{10}$ hydrocarbyl or halogen, $R^8$ is a $C_1$-$C_{10}$ hydrocarbyl, x, y and z each is an integer, $0 \leq x \leq 2$, $0 \leq y \leq 2$, $0 \leq z \leq 4$, and $x+y+z=4$.

Preferably, in a reaction for forming the solid catalyst component, relative to one mole of magnesium, the amount of the titanium compound used ranges from 0.5 to 120 moles, and preferably from 1 to 50 moles; the amount of the internal electron donor compound used ranges from 0 to 0.1 moles, and preferably ranges from 0 to 0.05 moles; and the amount of the auxiliary precipitant used ranges from 0 to 1 mole, and preferably from 0 to 0.7 moles.

Preferably, a molar ratio of the external electron donor compound to titanium in the solid catalyst component ranges from 0.05:1 to 50:1.

As for this subaspect, in embodiments where the solid catalyst component is the solid catalyst component of the present disclosure as described above, the preparation of the solid catalyst component is as described above.

As for this subaspect, in embodiments where the solid catalyst component is not the solid catalyst component of the present disclosure as described above but a solid catalyst component known in the art, the preparation of the solid catalyst component may be carried out according to the various processes taught in the art.

The solid catalyst component, the cocatalyst and the external electron donor compound of the catalyst system are introduced together into a polymerization reactor to initiate the polymerization of olefin(s), with or without a pre-contact between the solid catalyst component, the cocatalyst and the compound of the formula (I).

The olefin polymerization catalyst systems of the present disclosure, comprising the cyclotriveratrylene and derivatives thereof as an internal electron donor and/or an external electron donor, are suitable to homopolymerization or copolymerization of olefins. Examples of the olefin include, but are not limited to, ethylene, propylene, butene, 1-pentene, 1-hexene, 1-octene, 1-decene, 1-dodecene, 4-methyl-1-pentene.

Thus, in a third aspect, the present disclosure provides use of the above-described olefin polymerization catalyst in olefin polymerizations. A fourth aspect of the present disclosure provides an olefin polymerization process comprising: contacting an olefin monomer and an optional comonomer with the above-described olefin polymerization catalyst under polymerization conditions to form a polyolefin product and recovering the polyolefin product.

The olefin polymerization process and polymerization conditions employed therein are known per se. For example, the polymerization of olefin(s) may be carried out in liquid phase, or in gas phase, or in a combination of gas phase and liquid phase. The temperature for the polymerization may range from 0 to 150° C., and preferably from 60 to 90° C.

Examples of liquid phase polymerization medium include inert solvents such as saturated aliphatic hydrocarbons, aromatic hydrocarbons and the like, for example, isobutane, hexanes, heptanes, cyclohexane, naphtha, raffinate oils, hydrogenated gasolines, kerosenes, benzene, toluene, xylenes and the like.

In addition, hydrogen as a regulator of polymer molecular weight may be used to adjust the molecular weight of the resultant polymer.

In some embodiments, the olefin polymerization process comprises contacting ethylene and an optional comonomer such as an C3 to C12 α-olefin with the above-described olefin polymerization catalyst under polymerization conditions to form a polyethylene product and recovering the polyethylene product.

In other embodiments, the olefin polymerization process comprises contacting propylene and an optional comonomer such as ethylene or an C4 to C12 α-olefin with the above-described olefin polymerization catalyst under polymerization conditions to form a polypropylene product and recovering the polypropylene product.

A fifth aspect of the present disclosure provides the polyolefin products, for example, polyethylenes or polypropylenes, obtainable by the above-described olefin polymerization process.

EXAMPLES

The following examples are provided to further illustrate the present disclosure and by no means intend to limit the scope thereof.

In the following examples and comparative examples, unless specified otherwise, temperature values refer to degree Celsius, and pressure values refer to gauge pressure.

Testing Methods

1. Relative percentage by weight of titanium element in solid catalyst component: measured by spectrophotometry. The other compositional data of solid catalyst component: measured by liquid $^1$H-NMR.

2. Melt index (MI) of polymer: measured according to ASTM D1238-99, at 190° C. and 2.16 kg (or 21.6 Kg) load.

3. Content of copolymerized units for polymer powder: measured by liquid $^{13}$C-NMR.

4. Content by weight of hexane extractables for polymer powder: m grams of dried powder is placed in a Soxhlet's extractor and then extracted with hexane for 4 hours. The extracted powder is fully dried to afford n grams of powder. Then, the percentage by mass of the hexane extractables is: (m−n)/m*100%.

5. Melting enthalpy for polymer powder: a sample is subjected to a three-stage measurement on a Perkin Elmer DSC8500 differential scanning calorimeter under a measuring atmosphere of nitrogen gas as follows:

first stage: the sample is heated from 0 degree to 160 degree at a ramping rate of 10K/min and maintained at 160 degree for 5 min to eliminate heat history;

second stage: the sample is cooled from 160 degree to 0 degree at a cooling rate of 10K/min; and third stage: the sample is heated from 0 degree to 160 degree at a ramping rate of 10K/min.

The melting enthalpy of the temperature-rising profile in the third stage is taken as the measured result.

Both melting enthalpy and bulk density of a sample are determined by crystallinity. For polymer powders obtained under the identical copolymerization conditions (for example, identical comonomer type/concentration, reaction temperature/pressure/time, hydrogen gas-ethylene ratio and the like), polymer powders having a lower melting enthalpy will have a lower bulk density.

Preparation Examples 1-4 are to illustrate processes for preparing cyclotriveratrylene and derivatives thereof.

Preparation Example 1

Under ice bath condition, 1,2-dimethoxybenzene (1.0 g) was added dropwise into a mixture of a formaldehyde aqueous solution (4 mL, 38%), chloroform (0.1 mL) and concentrated hydrochloric acid (6 mL) and reaction was allowed to proceed. After 30 minutes, the solution became a paste, and the reaction mixture was continuously stirred at room temperature for 4 hours. The reaction mixture was filtrated to collect solids, and the solids were washed with chilled water and then thoroughly dried to afford 0.5 g of Compound A.

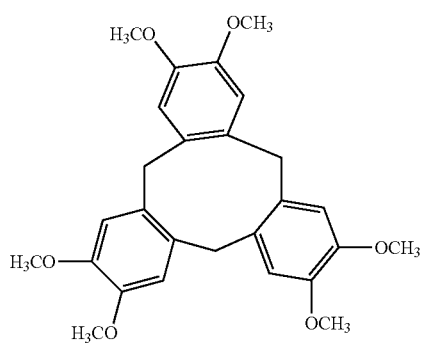

Compound A

Preparation Example 2

Under ice bath condition, 3-methoxy-4-bromine-benzyl alcohol (3.6 g) was dissolved in 30 mL of methanol. Under ice bath and stirring conditions, 15 mL of 65% perchloric acid was added dropwise into the above solution. Under nitrogen atmosphere, the reaction solution was stirred in ice bath for 18 h. 30 mL of water was slowly added into the reaction solution, and dichloromethane was then used to extract organic phase. The organic phase was carefully washed with a sodium hydroxide aqueous solution, followed by washing with deionized water. After having been dried, the organic phase was thoroughly evaporated under reduced pressure, and then purified through column chromatography to afford 0.8 g of Compound M.

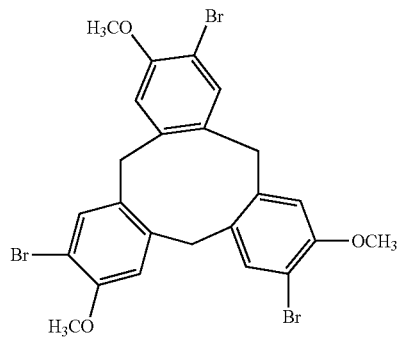

Compound M

Preparation Example 3

1,2-Diethoxybenzene (3.3 g) and triformol (0.63 g) were dissolved in dry dichloromethane (30 mL), and the resultant solution was stirred in an ice bath. Boron trifloride-diethyl ether (4.25 g) was slowly added dropwise to the above solution. Upon the completion of the addition, the ice-water bath was removed. The reaction solution was stirred at normal atmospheric temperature for 3 h, and the reaction was monitored by TLC (thin-layer chromatography) until the reaction was completed. The reaction was stopped, and the reaction solution was washed with water trice. An organic phase was separated by using a separating funnel, and then the organic solvent was thoroughly evaporated under reduced pressure to afford an oil. The oil was dissolved in a minor amount of acetone at first, and then a large amount of methanol was added thereto. The resultant mixture was placed in a refrigerator to precipitate white solids. The white solids were vacuum filtered and then thoroughly dried to afford 1.5 g of Compound B.

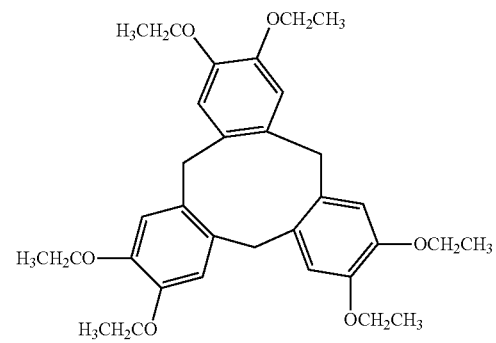

Compound B

Preparation Example 4

Under ice bath condition and nitrogen atmosphere, 3-methoxy-4-ethoxy-benzyl alcohol (3 g) was dissolved in 30 mL of methanol. Under ice bath and stirring conditions, 15 mL of 65% perchloric acid was added dropwise to the above solution, and then the reaction solution was continuously stirred in ice bath for 18 h. 30 mL of water was slowly added to the reaction solution, and then the organic phase was extracted with dichloromethane. The organic phase was washed with a sodium hydroxide aqueous solution and then with deionized water. After having been dried, the organic phase was thoroughly evaporated under reduced pressure, and then purified through column chromatography to afford 1.0 g of Compound F.

Compound F

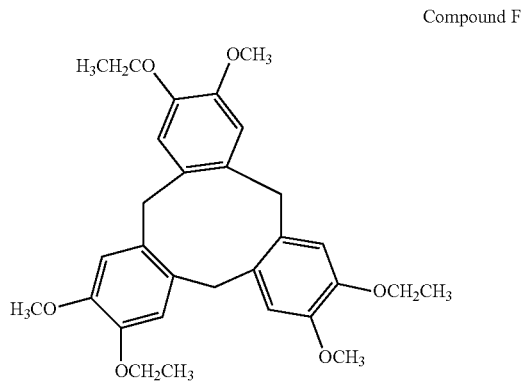

Examples 1-5 are to illustrate use of cyclotriveratrylene and derivatives thereof as an internal electron donor in catalysts for ethylene polymerization.

Example 1

(1) Preparation of Solid Catalyst Component A

To a reactor, in which air had been fully replaced with high pure $N_2$, were successively charged with 6.0 g of spherical support $MgCl_2.2.6C_2H_5OH$ and 120 mL of toluene, and the reaction mixture was cooled with stirring to −10° C. To the reaction mixture was added dropwise 50 mL of triethyl aluminum solution in hexane (1.0 M) and then 0.15 g of Compound A, and the mixture was warmed to 50° C. and maintained at that temperature for 3 hours. The stirring in the reactor was stopped, the reaction mixture was let stand, and solid particles precipitated quickly. A supernatant was sucked out, and precipitants were washed sequentially with toluene and hexane several times. 120 mL of hexane was added to the reactor containing the solid particles, and the reaction mixture was cooled with stirring to 0° C. 6 mL of titanium tetrachloride was slowly added dropwise to the above reaction mixture, thereafter the temperature was enhanced to 60° C. and maintained for 2 hours. The stirring in the reactor was stopped, the reaction mixture was let stand, and solid particles precipitated quickly. A supernatant was sucked out, and precipitants were washed with hexane twice, then transferred by means of hexane to a fritted glass filter, and dried with a high pure nitrogen flow, to afford solid spherical catalyst component a having good flowability, of which composition is shown in Table 1 below.

(2) Homopolymerization (i) Polymerization at Low Hydrogen Gas-Ethylene Ratio

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 75° C., hydrogen gas was introduced to bring the pressure inside the reactor to 0.28 MPa (gauge), and then ethylene was introduced to bring the total pressure inside the reactor to 1.03 MPa (gauge). The polymerization was allowed to continue at 85° C. for 2 hours, with ethylene being continuously introduced into the reactor to maintain the total pressure at 1.03 MPa (gauge). Polymerization results are shown in Table 2 below.

(ii) Polymerization at High Hydrogen Gas-Ethylene Ratio

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 75° C., hydrogen gas was introduced to bring the pressure inside the reactor to 0.68 MPa, and then ethylene was introduced to bring the total pressure inside the reactor to 1.03 MPa. The polymerization was allowed to continue at 85° C. for 2 hours, with ethylene being continuously introduced into the reactor to maintain the total pressure at 1.03 MPa. Polymerization results are shown in Table 2 below.

Comparative Example 1-1

(1) Preparation of Solid Catalyst Component D1-1

To a reactor, in which air had been fully replaced with high pure $N_2$, were successively charged with 6.0 g of spherical support $MgCl_2.2.6C_2H_5OH$ and 120 mL of toluene, and the reaction mixture was cooled with stirring to −10° C. To the reaction mixture was added dropwise 50 mL of triethyl aluminum solution in hexane (1.0 M), and the mixture was warmed to 50° C. and maintained at that temperature for 3 hours. The stirring in the reactor was stopped, the reaction mixture was let stand, and solid particles precipitated quickly. A supernatant was sucked out, and precipitants were washed sequentially with toluene and hexane several times. 120 mL of hexane was added to the reactor containing the solid particles, and the reaction mixture was cooled with stirring to 0° C. 6 mL of titanium tetrachloride was slowly added dropwise to the above reaction mixture, thereafter the temperature was enhanced to 60° C. and maintained for 2 hours. The stirring in the reactor was stopped, the reaction mixture was let stand, and solid particles precipitated quickly. A supernatant was sucked out, and precipitants were washed with hexane twice, then transferred by means of hexane to a fritted glass filter, and dried with a high pure nitrogen flow, to afford solid spherical catalyst component D1-1 having good flowability, of which composition is shown in Table 1 below.

(2) Homopolymerization

The polymerization procedure is the same as described in Example 1, except that the solid catalyst component D1-1 prepared in Comparative Example 1-1 was used. Polymerization results are shown in Table 2 below.

Comparative Example 1-2

(1) Preparation of Solid Catalyst Component D1-2

To a reactor, in which air had been fully replaced with high pure $N_2$, were successively charged with 6.0 g of spherical support $MgCl_2.2.6C_2H_5OH$ and 120 mL of toluene, and the reaction mixture was cooled with stirring to −10° C. To the reaction mixture was added dropwise 50 mL of triethyl aluminum solution in hexane (1.0 M) and then 1.5 mL of ethyl benzoate, and the mixture was warmed to 50° C. and maintained at that temperature for 3 hours. The stirring in the reactor was stopped, the reaction mixture was let stand, and solid particles precipitated quickly. A supernatant was sucked out, and precipitants were washed sequentially with toluene and hexane several times. 120 mL of hexane was added to the reactor containing the solid particles, and the reaction mixture was cooled with stirring to 0° C. 6 mL of titanium tetrachloride was slowly added dropwise to the above reaction mixture, thereafter the temperature was enhanced to 60° C. and maintained for 2 hours. The stirring in the reactor was stopped, the reaction mixture was let stand, and solid particles precipitated quickly. A supernatant was sucked out, and precipitants were washed with hexane twice, then transferred by means of hexane to a fritted glass filter, and dried with a high pure nitrogen flow, to afford solid spherical catalyst component D1-2 having good flowability, of which composition is shown in Table 1 below.

(2) Homopolymerization

The polymerization procedure is the same as described in Example 1, except that the solid catalyst component D1-2 prepared in Comparative Example 1-2 was used. Polymerization results are shown in Table 2 below.

TABLE 2

| | Polymerization results | | | |
|---|---|---|---|---|
| | 0.28 MPa $H_2$/ 0.75 MPa ethylene | | 0.68 MPa $H_2$/ 0.35 MPa ethylene | |
| Catalyst | Activity | Melt index (21.6 Kg) | Activity | Melt index (2.16 Kg) |
| Ex. 1 | 31900 | 194 | 13000 | 409 |
| Comp. Ex. 1-1 | 23400 | 107 | 6100 | 90 |
| Comp. Ex. 1-2 | 30000 | 120 | 6200 | 282 |

As shown in Table 2, when a cyclotriveratrylene derivative is introduced into the solid catalyst component a (Example 1), catalyst activity under polymerization condition of high hydrogen gas-ethylene ratio is significantly higher than that for the comparative examples, and the melt index for the polymer powder is also significantly higher than that for the comparative examples.

Furthermore, as shown in Table 2, when the cyclotriveratrylene derivative is introduced, as an internal electron donor, into the solid catalyst component, catalyst activity and melt index for polymer powder under polymerization condition of low hydrogen gas-ethylene ratio are also enhanced.

Example 2

(1) Preparation of Solid Catalyst Component B

To a reactor, in which air had been fully replaced with high pure $N_2$, were successively charged with 4.0 g of magnesium dichloride, 50 mL of toluene, 3.0 mL of epoxy chloropropane, 9 mL of tri-n-butyl phosphate, 4.4 mL of ethanol and 0.2 g of Compound A. The reaction mixture was heated with stirring to 70° C. and maintained at that temperature for 2 hours. The reaction mixture was cooled to −10° C., and then 70 mL of titanium tetrachloride was slowly added dropwise, followed by the dropwise-addition of 5 mL of tetraethoxy silicane. Next, the temperature was gradually enhanced to 85° C. and maintain for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid spherical catalyst component b having good flowability, of which composition is shown in Table 1 below.

(2) Homopolymerization (i) Polymerization at Low Hydrogen Gas-Ethylene Ratio

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 70° C., hydrogen gas was introduced to bring the pressure inside the reactor to 0.28 MPa (gauge), and then ethylene was introduced to bring the total pressure inside the reactor to 0.73 MPa (gauge). The polymerization was allowed to continue at 80° C. for 2 hours, with ethylene being continuously introduced into the reactor to maintain the total pressure at 0.73 MPa (gauge). Polymerization results are shown in Table 3 below.

(ii) Polymerization at High Hydrogen Gas-Ethylene Ratio

To a 2 L stainless steel reactor, in which air had been fully replaced with high pure $N_2$, were charged 1 L of hexane and 1.0 mL of 1M triethyl aluminum solution, followed by the addition of the solid catalyst component (containing 0.6 mg of titanium) prepared by the above-described process. The reactor was heated with stirring to 70° C., hydrogen gas was introduced to bring the pressure inside the reactor to 0.60 MPa (gauge), and then ethylene was introduced to bring the total pressure inside the reactor to 1.00 MPa (gauge). The polymerization was allowed to continue at 90° C. for 2 hours, with ethylene being continuously introduced into the reactor to maintain the total pressure at 1.00 MPa (gauge). Polymerization results are shown in Table 3 below.

(3) Ethylene-Butene Copolymerization

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 70° C., hydrogen gas was introduced to bring the pressure inside the reactor to 0.28 MPa (gauge), and then ethylene/butene mixed gases (having a molar ratio of 0.75:0.25) was introduced to bring the total pressure inside the reactor to 0.73 MPa (gauge). The polymerization was allowed to continue at 80° C. for 0.5 hours, with the ethylene/butene mixed gases being continuously introduced into the reactor to maintain the total pressure at 0.73 MPa (gauge). Polymerization results are shown in Table 4 below.

(4) Ethylene-Hexene Copolymerization

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 70° C., 20 mL of hexene was added thereinto, hydrogen gas was introduced to bring the pressure inside the reactor to 0.28 MPa (gauge), and then ethylene was introduced to bring the total pressure inside the reactor to 0.73 MPa (gauge). The polymerization was allowed to continue at 80° C. for 0.5 hours, with the ethylene being continuously introduced into the reactor to maintain the total pressure at 0.73 MPa (gauge). Polymerization results are shown in Table 5 below.

Comparative Example 2

(1) Preparation of Solid Catalyst Component D2

To a reactor, in which air had been fully replaced with high pure $N_2$, were successively charged 4.0 g of magnesium dichloride, 50 mL of toluene, 3.0 mL of epoxy chloropropane, 9 mL of tri-n-butyl phosphate, and 4.4 mL of ethanol. The reaction mixture was heated with stirring to 70° C. and maintained at that temperature for 2 hours. The reaction mixture was cooled to −10° C., and then 70 mL of titanium tetrachloride was slowly added dropwise, followed by the dropwise-addition of 5 mL of tetraethoxy silicane. Next, the temperature was gradually enhanced to 85° C. and maintain for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component D2 having good flowability, of which composition is shown in Table 1 below.

(2) Homopolymerization

The polymerization procedure is the same as described in Example 2, except that the solid catalyst component D2 prepared in Comparative Example 2 was used. Polymerization results are shown in Table 3 below.

(3) Ethylene-Butene Copolymerization

The polymerization procedure is the same as described in Example 2, except that the solid catalyst component D2 prepared in Comparative Example 2 was used. Polymerization results are shown in Table 4 below.

(4) Ethylene-Hexene Copolymerization

The polymerization procedure is the same as described in Example 2, except that the solid catalyst component D2 prepared in Comparative Example 2 was used. Polymerization results are shown in Table 5 below.

TABLE 3

Homopolymerization results

| Catalyst | 0.28 MPa $H_2$/ 0.45 MPa ethylene | | 0.60 MPa $H_2$/ 0.40 MPa ethylene | |
|---|---|---|---|---|
| | Activity | Melt index (2.16 Kg) | Activity | Melt index (2.16 Kg) |
| Ex. 2 | 35000 | 1.1 | 22000 | 51 |
| Comp. Ex. 2 | 30000 | 0.5 | 15000 | 30 |

As shown in Table 3, when a cyclotriveratrylene derivative is introduced into the solid catalyst component b (Example 2), catalyst activity under polymerization condition of high hydrogen gas-ethylene ratio is significantly higher than that for the comparative example, and the melt index of the polymer powder is also significantly higher than that for the comparative example.

Also, as shown in Table 3, when the cyclotriveratrylene derivative is introduced, as an internal electron donor, into the solid catalyst component, catalyst activity and melt index of polymer powder under polymerization condition of low hydrogen gas-ethylene ratio may also be enhanced.

TABLE 4

Ethylene-butene copolymerization results (powder)

| | Melting enthalpy | Content of copolymerized units |
|---|---|---|
| Example 2 | 139 J/g | 3.0 mol % |
| Comparative Example 2 | 146 J/g | 4.2 mol % |

As shown in Table 4, when the cyclotriveratrylene derivative is introduced into the solid catalyst component b of Example 2, in ethylene/butene copolymerization, the resultant polymerization product can have a lower melting enthalpy (i.e., lower density) at a lower content of copolymerized units. This suggests that the copolymerized units in the polymerization product of Example 2 are more uniformly distributed.

TABLE 5

Ethylene-hexene copolymerization results (powder)

| | Melting enthalpy | Content of copolymerized units | Hexane extractables |
|---|---|---|---|
| Ex. 2 | 176 J/g | 0.75 mol % | 3.9 wt % |
| Comp. Ex. 2 | 179 J/g | 0.68 mol % | 4.1 wt % |

As shown in Table 5, when the cyclotriveratrylene derivative is introduced into the solid catalyst component b of Example 2, in ethylene/hexene copolymerization, the resultant polymerization product has a lower melting enthalpy (i.e., lower density). Furthermore, even though the polymerization product of Example 2 has a higher content of copolymerized units, it has less hexane extractables. This suggests that the copolymerized units in the polymerization product of Example 2 are more uniformly distributed.

Example 3

(1) Preparation of Solid Catalyst Component C

To a reactor, in which air had been fully replaced with high pure $N_2$, were successively charged 4.0 g of magnesium dichloride, 50 mL of toluene, 3.0 mL of epoxy chloropropane, 9 mL of tri-n-butyl phosphate, and 4.4 mL of ethanol. The reaction mixture was heated with stirring to 70° C. and maintained at that temperature for 2 hours. The reaction mixture was cooled to −10° C., and then 65 mL of titanium tetrachloride was slowly added dropwise, followed by the dropwise-addition of 4 mL of tetraethoxy silicane. Next, the temperature was gradually enhanced to 85° C. and maintain for 1 hour. 0.2 g of Compound B was added to the reactor, and the reactor was maintained at 85° C. for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component c having good flowability, of which composition is shown in Table 1 below.

(2) Homopolymerization (i) Polymerization at Low Hydrogen Gas-Ethylene Ratio

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 70° C., hydrogen gas was introduced to bring the pressure inside the reactor to 0.28 MPa (gauge), and then ethylene was introduced to bring the total pressure inside the reactor to 0.73 MPa (gauge). The polymerization was allowed to continue at 80° C. for 2 hours, with ethylene being continuously introduced into the reactor to maintain the total pressure at 0.73 MPa (gauge). Polymerization results are shown in Table 6 below.

(ii) Polymerization at High Hydrogen Gas-Ethylene Ratio

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 70° C., hydrogen gas was introduced to bring the pressure inside the reactor to 0.58 MPa (gauge), and then ethylene was introduced to bring the total pressure inside the reactor to 0.73 MPa (gauge). The polymerization was allowed to continue at 80° C. for 2 hours, with ethylene being continuously introduced into the reactor to maintain the total pressure at 0.73 MPa (gauge). Polymerization results are shown in Table 6 below.

Comparative Example 3

(1) Preparation of Solid Catalyst Component D3

To a reactor, in which air had been fully replaced with high pure $N_2$, were successively charged 4.0 g of magnesium dichloride, 50 mL of toluene, 3.0 mL of epoxy chloropropane, 9 mL of tri-n-butyl phosphate, and 4.4 mL of ethanol. The reaction mixture was heated with stirring to 70° C. and maintained at that temperature for 2 hours. The reaction mixture was cooled to −10° C., and then 65 mL of titanium tetrachloride was slowly added dropwise, followed by the dropwise-addition of 4 mL of tetraethoxy silicane. Next, the temperature was gradually enhanced to 85° C. and maintain for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component D3 having good flowability, of which composition is shown in Table 1 below.

(2) Homopolymerization

The polymerization procedure is the same as described in Example 3, except that the solid catalyst component D3 prepared in Comparative Example 3 was used. Polymerization results are shown in Table 6 below.

TABLE 6

| | Homopolymerization results | | | |
|---|---|---|---|---|
| | 0.28 MPa $H_2$/ 0.45 MPa ethylene | | 0.58 MPa $H_2$/ 0.15 MPa ethylene | |
| Catalyst | Activity | Melt index (2.16 Kg) | Activity | Melt index (2.16 Kg) |
| Example 3 | 30800 | 1.2 | 4800 | 209 |
| Comparative Example 3 | 30900 | 1.2 | 3600 | 189 |

As shown in Table 6, when a cyclotriveratrylene derivative is introduced into the solid catalyst component c of Example 3, both catalyst activity and melt index of polymer powder under polymerization condition of high hydrogen gas-ethylene ratio are significantly higher than those for the comparative example.

Example 4a (1) Preparation of Solid Catalyst Component D1

To a reactor, in which air had been fully replaced with high pure $N_2$, were successively charged 4.0 g of magnesium dichloride, 80 mL of toluene, 3.5 mL of epoxy chloropropane, and 13 mL of tri-n-butyl phosphate. The reaction mixture was heated with stirring to 60° C. and maintained at that temperature for 2 hours. 1.4 g of phthalic anhydride was added to the reactor, and the reactor was maintained at 60° C. for 1 hour. The reaction mixture was cooled to −30° C., and then 60 mL of titanium tetrachloride was slowly added dropwise. Next, the temperature was gradually enhanced to 85° C. and maintain for 1 hour. 0.15 g of Compound A was added to the reactor, and the reactor was maintained at 85° C. for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component d1 having good flowability, of which composition is shown in Table 1 below.

(2) Homopolymerization

The polymerization procedure is the same as described in Example 1, except that the solid catalyst component d1 prepared in Example 4a was used. Polymerization results are shown in Table 7 below.

Example 4b

(1) Preparation of Solid Catalyst Component D2

To a reactor, in which air had been fully replaced with high pure $N_2$, were successively charged 4.0 g of magnesium dichloride, 80 mL of toluene, 3.5 mL of epoxy chloropropane, and 13 mL of tri-n-butyl phosphate. The reaction mixture was heated with stirring to 60° C. and maintained at that temperature for 2 hours. 1.4 g of phthalic anhydride was added to the reactor, and the reactor was maintained at 60° C. for 1 hour. The reaction mixture was cooled to −30° C., and then 60 mL of titanium tetrachloride was slowly added dropwise. Next, the temperature was gradually enhanced to 85° C. and maintain for 1 hour. 0.1 g of Compound B was added to the reactor, and the reactor was maintained at 85° C. for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component d2 having good flowability, of which composition is shown in Table 1 below.

(2) Homopolymerization

The polymerization procedure is the same as described in Example 1, except that the solid catalyst component d2 prepared in Example 4b was used. Polymerization results are shown in Table 7 below.

(3) Copolymerization

To a 2 L stainless steel reactor, in which air had been fully replaced with high pure $N_2$, were charged 1 L of hexane and 1.0 mL of 1 M triethyl aluminum solution, followed by the addition of the solid catalyst component (containing 0.6 mg of titanium) prepared by the above-described process. The reactor was heated with stirring to 75° C., 20 ml of hexene was added thereinto, hydrogen gas was introduced to bring the pressure inside the reactor to 0.28 MPa (gauge), and then ethylene was introduced to bring the total pressure inside the reactor to 1.03 MPa (gauge). The polymerization was allowed to continue at 85° C. for 0.5 hours, with the ethylene being continuously introduced into the reactor to maintain the total pressure at 1.03 MPa (gauge). Polymerization results are shown in Table 8 below.

Comparative Example 4

(1) Preparation of Solid Catalyst Component D4

To a reactor, in which air had been fully replaced with high pure $N_2$, were successively charged 4.0 g of magnesium dichloride, 80 mL of toluene, 3.5 mL of epoxy chloropropane, and 13 mL of tri-n-butyl phosphate. The reaction mixture was heated with stirring to 60° C. and maintained at that temperature for 2 hours. 1.4 g of phthalic anhydride was added to the reactor, and the reactor was maintained at 60° C. for 1 hour. The reaction mixture was cooled to −30° C., and then 60 mL of titanium tetrachloride was slowly added dropwise. Next, the temperature was gradually enhanced to 85° C. and maintain for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component D4 having good flowability, of which composition is shown in Table 1 below.

(2) Homopolymerization

The polymerization procedure is the same as described in Example 1, except that the solid catalyst component D4 prepared in Comparative Example 4 was used. Polymerization results are shown in Table 7 below.

(3) Copolymerization

The polymerization procedure is the same as described in Example 4b, except that the solid catalyst component D4 prepared in Comparative Example 4 was used. Polymerization results are shown in Table 8 below.

TABLE 7

| | Homopolymerization results | | | |
|---|---|---|---|---|
| | 0.28 MPa $H_2$/ 0.75 MPa ethylene | | 0.68 MPa $H_2$/ 0.35 MPa ethylene | |
| Catalyst | Activity | Melt index (21.6 Kg) | Activity | Melt index (2.16 Kg) |
| Example 4a | 33000 | 13.6 | 5400 | 70 |
| Example 4b | — | — | 6200 | 55 |
| Comparative Example 4 | 32000 | 14.6 | 3900 | 52 |

As shown in Table 7, when a cyclotriveratrylene derivative is introduced into the solid catalyst component d1/d2 of Example 4a/4b, both catalyst activity and melt index of polymer powder under polymerization condition of high hydrogen gas-ethylene ratio are higher than those for the comparative example.

TABLE 8

| Ethylene-hexene copolymerization results (powder) | |
|---|---|
| | Melting enthalpy |
| Example 4b | 181 J/g |
| Comparative Example 4 | 184 J/g |

As shown in Table 8, when a cyclotriveratrylene derivative is introduced into the solid catalyst component d2 of Example 4b, in ethylene/hexene copolymerization, the resultant polymerization product has a lower melting enthalpy (i.e., lower density) than that for Comparative Example 4.

Example 5

(1) Preparation of Solid Catalyst Component E

To a reactor, in which air had been fully replaced with high pure $N_2$, were successively charged 2.0 g of magnesium dichloride, 80 mL of toluene, 2 mL of epoxy chloropropane, and 6 mL of tri-n-butyl phosphate. The reaction mixture was heated with stirring to 60° C. and maintained at that temperature for 2 hours. The reaction mixture was cooled to −30° C., and then 30 mL of titanium tetrachloride was slowly added dropwise. Next, the temperature was gradually enhanced to 85° C. and maintain for 1 hour. 0.1 g of Compound A was added to the reactor, and the reactor was maintained at 85° C. for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component e having good flowability, of which composition is shown in Table 1 below.

(2) Homopolymerization

The polymerization procedure is the same as described in Example 1, except that the solid catalyst component e prepared in Example 5 was used. Polymerization results are shown in Table 9 below.

(3) Ethylene-Butene Copolymerization

The polymerization procedure is the same as described in Example 2, except that the solid catalyst component e prepared in Example 5 was used. Polymerization results are shown in Table 10 below.

Comparative Example 5

(1) Preparation of Solid Catalyst Component D5

To a reactor, in which air had been fully replaced with high pure $N_2$, were successively charged 2.0 g of magnesium dichloride, 80 mL of toluene, 2 mL of epoxy chloropropane, and 6 mL of tri-n-butyl phosphate. The reaction mixture was heated with stirring to 60° C. and maintained at that temperature for 2 hours. The reaction mixture was cooled to −30° C., and then 30 mL of titanium tetrachloride was slowly added dropwise. Next, the temperature was gradually enhanced to 85° C. and maintain for 1 hour. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component D5 having good flowability, of which composition is shown in Table 1 below.

(2) Homopolymerization

The polymerization procedure is the same as described in Example 1, except that the solid catalyst component D5 prepared in Comparative Example 5 was used. Polymerization results are shown in Table 9 below.

(3) Ethylene-Butene Copolymerization

The polymerization procedure is the same as described in Example 2, except that the solid catalyst component D5 prepared in Comparative Example 5 was used. Polymerization results are shown in Table 10 below.

TABLE 9

Homopolymerization results

| Catalyst | 0.28 MPa $H_2$/ 0.75 MPa ethylene | | 0.68 MPa $H_2$/0 .35 MPa ethylene | |
|---|---|---|---|---|
| | Activity | Melt index (21.6 Kg) | Activity | Melt index (2.16 Kg) |
| Example 5 | 28100 | 24.2 | 8400 | 111 |
| Comparative Example 5 | 27400 | 35.1 | 7800 | 53 |

As shown in Table 9, when a cyclotriveratrylene derivative is introduced into the solid catalyst component e of Example 5, catalyst activity under polymerization condition of high hydrogen gas-ethylene ratio is higher than that for the comparative example, and the melt index of the polymer powder is significantly higher than that for the comparative example.

TABLE 10

Ethylene-butene copolymerization results (powder)

| | Melting enthalpy | Hexane extractables |
|---|---|---|
| Example 5 | 127 J/g | 26.4 mol % |
| Comparative Example 5 | 139 J/g | 35.4 mol % |

As shown in Table 10, when a cyclotriveratrylene derivative is introduced into the solid catalyst component e of Example 5, in ethylene//butene copolymerization, not only can the resultant polymerization product have a lower melting enthalpy (i.e., lower density), but also it has less hexane extractables. This suggests that the copolymerized units in the polymerization product of Example 5 are more uniformly distributed.

Examples 6-8 are to illustrate use of cyclotriveratrylene and derivatives thereof as an external electron donor in ethylene polymerization catalysts.

Example 6

(1) Preparation of Solid Catalyst Component F

The preparation procedure of the solid catalyst component is the same as described in Comparative Example 4.

(2) Ethylene-Butene Copolymerization

To a 2 L stainless steel reactor, in which air had been fully replaced with high pure $N_2$, were charged 1 L of hexane and 1.0 mL of 1 M triethyl aluminum solution, followed by the addition of 25 mg of the solid catalyst component prepared by the above-described process and 40 mg of Compound A. The reactor was heated with stirring to 70° C., hydrogen gas was introduced to bring the pressure inside the reactor to 0.28 MPa (gauge), and then ethylene/butene mixed gases (having a molar ratio of 0.935:0.065) was introduced to bring the total pressure inside the reactor to 0.73 MPa (gauge). The polymerization was allowed to continue at 80° C. for 0.5 hours, with the ethylene/butene mixed gases being continuously introduced into the reactor to maintain the total pressure at 0.73 MPa (gauge). Polymerization results are shown in Table 11 below.

Comparative Example 6

(1) Preparation of Solid Catalyst Component F

The preparation procedure of the solid catalyst component is the same as described in Comparative Example 4.

(2) Ethylene-Butene Copolymerization

The polymerization procedure is the same as described in Example 6, except that the Compound A was omitted. Polymerization results are shown in Table 11 below.

TABLE 11

| Ethylene-butene copolymerization results (powder) | | |
| --- | --- | --- |
|  | Melting enthalpy | Content of copolymerized units |
| Example 6 | 166 J/g | 1.0 mol % |
| Comparative Example 6 | 170 J/g | 1.1 mol % |

As shown in Table 11, when a cyclotriveratrylene derivative is introduced as an external electron donor into the polymerization system of Example 6, in ethylene/butene copolymerization, the resultant polymerization product can have a lower melting enthalpy (i.e., lower density) even at a lower content of copolymerized units. This suggests that the copolymerized units in the polymerization product of Example 6 are more uniformly distributed.

Example 7

(1) Preparation of Solid Catalyst Component G

The preparation procedure of the solid catalyst component is the same as described in Comparative Example 2.

(2) Ethylene-Butene Copolymerization

To a 2 L stainless steel reactor, in which air had been fully replaced with high pure $N_2$, were charged 1 L of hexane and 1.0 mL of 1 M triethyl aluminum solution, followed by the addition of 24 mg of the solid catalyst component prepared by the above-described process and 42 mg of Compound A. The reactor was heated with stirring to 70° C., hydrogen gas was introduced to bring the pressure inside the reactor to 0.28 MPa (gauge), and then ethylene/butene mixed gases (having a molar ratio of 0.75:0.25) was introduced to bring the total pressure inside the reactor to 0.73 MPa (gauge). The polymerization was allowed to continue at 80° C. for 0.5 hours, with the ethylene/butene mixed gases being continuously introduced into the reactor to maintain the total pressure at 0.73 MPa (gauge). Polymerization results are shown in Table 12 below.

Comparative Example 7

(1) Preparation of Solid Catalyst Component G

The preparation procedure of the solid catalyst component is the same as described in Comparative Example 2.

(2) Ethylene-Butene Copolymerization

The polymerization procedure is the same as described in Example 7, except that 42 mg of ethyl benzoate was used to replace for the 42 mg of Compound A. Polymerization results are shown in Table 12 below.

TABLE 12

| Ethylene-butene copolymerization results (powder) | | |
| --- | --- | --- |
|  | Melting enthalpy | Content of copolymerized units |
| Example 7 | 153 J/g | 1.9 mol % |
| Comparative Example 7 | 165 J/g | 1.4 mol % |

As shown in Table 12, compared to the ethyl benzoate used in Comparative Example 7, when a cyclotriveratrylene derivative is introduced as an external electron donor into the polymerization system of Example 7, the resultant polymerization product can have a lower melting enthalpy (i.e., lower density).

Example 8

(1) Preparation of Solid Catalyst Component H

To a reactor, in which air had been fully replaced with high pure $N_2$, were successively charged 4.0 g of magnesium dichloride, 50 mL of toluene, 3.3 mL of epoxy chloropropane, 8 mL of tri-n-butyl phosphate, and 4.4 mL of ethanol. The reaction mixture was heated with stirring to 68° C. and maintained at that temperature for 2 hours. The reaction mixture was cooled to −10° C., and then 65 mL of titanium tetrachloride was slowly added dropwise, followed by the dropwise-addition of 6 mL of tetraethoxy silicane. Next, the temperature was gradually enhanced to 85° C. and maintain for 2 hours. The stirring in the reactor was stopped, the reaction mixture was let stand, and solid particles precipitated quickly. A supernatant was sucked out, and precipitants were washed sequentially with toluene and hexane several times, then transferred by means of hexane to a fritted glass filter, and dried with a high pure nitrogen flow, to afford solid catalyst component h having good flowability, of which composition is shown in Table 1 below.

(2) Ethylene-Hexene Copolymerization

To a 2 L stainless steel reactor, in which air had been fully replaced with high pure $N_2$, were charged 1 L of hexane and 1.0 mL of 1 M triethyl aluminum solution, followed by the addition of 11 mg of the solid catalyst component prepared by the above-described process and 11 mg of Compound A. The reactor was heated with stirring to 70° C., 20 ml of hexene was added thereinto, hydrogen gas was introduced to bring the pressure inside the reactor to 0.28 MPa (gauge), and then ethylene was introduced to bring the total pressure inside the reactor to 0.73 MPa (gauge). The polymerization was allowed to continue at 80° C. for 0.5 hours, with the ethylene being continuously introduced into the reactor to maintain the total pressure at 0.73 MPa (gauge). Polymerization results are shown in Table 13 below.

Comparative Example 8

(1) Preparation of Solid Catalyst Component H

The preparation procedure of the solid catalyst component is the same as described in Example 8.

(2) Ethylene-Hexene Copolymerization

The polymerization procedure is the same as described in Example 8, except that the Compound A was omitted. Polymerization results are shown in Table 13 below.

TABLE 13

Ethylene-hexene copolymerization results (powder)

| | Melting enthalpy | Hexane extractables |
|---|---|---|
| Example 8 | 186 J/g | 1.1 wt % |
| Comparative Example 8 | 186 J/g | 2.4 wt % |

As shown in Table 13, when a cyclotriveratrylene derivative is introduced as an external electron donor into the polymerization system of Example 8, in ethylene/hexene copolymerization, although the resultant polymer powder has a melting enthalpy that is not lower than that of Comparative Example 8, its hexane extractables are relatively reduced. Such a property is in favor of stable production in industry.

Examples 9-10 are to illustrate use of cyclotriveratrylene and derivatives thereof as an internal electron donor in catalysts for propylene polymerization.

Example 9

(1) Preparation of Solid Catalyst Component I

To a 300 ml glass reactor equipped with a stirrer, in which reactor air had been fully replaced with high pure $N_2$, were successively charged 50 ml of titanium tetrachloride and 40 ml of hexane, and the contents were cooled with stirring to −20° C. To the above solution was added 9 g of spherical magnesium dichloride-alcohol adduct ($MgCl_2.2.6C_2H_5OH$, prepared from magnesium dichloride and ethanol according to process described in CN1330086A). The reaction mixture was slowly heated stagewise with stirring, with 0.25 mmol of Compound A, 5 mmol of di-isobutyl phthalate (DIBP) and 20 ml of toluene being added thereto during the heating, and then the temperature was enhanced to 110° C. and maintained at that temperature for 0.5 hours. The stirring in the reactor was stopped, the reaction mixture was let stand, and solid phase precipitated quickly. A supernatant was sucked out, and the solid phase left in the glass reactor was treated with 80 mL of titanium tetrachloride twice, washed with hexane five times, and dried under vacuum, to afford spherical solid catalyst component i, of which composition is shown in Table 1 below.

(2) Propylene Polymerization

A 5 L autoclave was purged with nitrogen gas flow, and then under nitrogen atmosphere, 0.25 mmol of triethylaluminum, 0.01 mmol of cyclohexyl methyl dimethoxy silane (CHMMS), 10 ml of anhydrous hexane and 10 mg of the spherical catalyst component i were introduced thereto. The autoclave was closed, and then 1.2 NL (standard volume) of hydrogen gas and 2.3 L of liquid propylene were introduced to the autoclave. The temperature inside the autoclave was brought to 70° C., and the polymerization was allowed to continue for 1.0 hours. Polymerization results are shown in Table 14 below.

Comparative Example 9

(1) Preparation of Solid Catalyst Component D9

The spherical solid catalyst component D9 was prepared by the procedure as described for Example 9, except that the Compound A was omitted. The composition of the solid catalyst component is shown in Table 1 below.

(2) Propylene Polymerization

The polymerization procedure is the same as described in Example 9, except that the solid catalyst component D9 prepared in Comparative Example 9 was used. Polymerization results are shown in Table 14 below.

TABLE 14

Propylene polymerization results

| No. | Activity (KgPP/gcat · h) | MI (g/10 min) | II (wt %) |
|---|---|---|---|
| Example 9 | 53.7 | 4.7 | 97.3 |
| Comparative Example 9 | 40.3 | 4.8 | 97.1 |

As shown in Table 14, when a cyclotriveratrylene derivative is introduced into the solid catalyst component i of Example 9, the polymerization activity of the catalyst is significantly enhanced, and the isotacticity of the polymer powder can meet the requirements of applications.

Example 10

(1) Preparation of Solid Catalyst Component J

To a 300 ml glass reactor equipped with a stirrer, in which reactor air had been fully replaced with high pure $N_2$, were successively charged 50 ml of titanium tetrachloride and 40 ml of hexane, and the contents were cooled with stirring to −20° C. To the above solution was added 9 g of spherical magnesium dichloride-alcohol adduct ($MgCl_2.2.6C_2H_5OH$, prepared from magnesium dichloride and ethanol according to process described in CN1330086A). The reaction mixture was slowly heated stagewise with stirring, with 0.25 mmol of Compound A, 5 mmol of di-n-butyl phthalate (DNBP) and 20 ml of toluene being added thereto during the heating, and then the temperature was enhanced to 110° C. and maintained at that temperature for 0.5 hours. The stirring in the reactor was stopped, the reaction mixture was let stand, and solid phase precipitated quickly. A supernatant was sucked out, and the solid phase left in the reactor was treated with 80 mL of titanium tetrachloride twice, washed with hexane five times, and dried under vacuum, to afford spherical solid catalyst component j, of which composition is shown in Table 1 below.

(2) Propylene Polymerization

The polymerization procedure is the same as described in Example 9, except that the solid catalyst component j prepared in Example 10 was used. Polymerization results are shown in Table 15 below.

Comparative Example 10

(1) Preparation of Solid Catalyst Component D10

The spherical solid catalyst component D10 was prepared by the procedure as described for Example 10, except that the Compound A was omitted. The composition of the solid catalyst component is shown in Table 1 below.

(2) Propylene Polymerization

The polymerization procedure is the same as described in Example 9, except that the solid catalyst component D10 prepared in Comparative Example 10 was used. Polymerization results are shown in Table 15 below.

TABLE 15

Propylene polymerization results

| No. | Activity (KgPP/gcat · h) | MI (g/10 min) | II (wt %) |
|---|---|---|---|
| Example 10 | 52.6 | 4.6 | 98.2 |
| Comparative Example 10 | 39.8 | 4.5 | 98.3 |

As shown in Table 15, when a cyclotriveratrylene derivative is introduced into the solid catalyst component j of Example 10, the polymerization activity of the catalyst is significantly enhanced, and the isotacticity of the polymer powder can meet the requirements of applications.

Example 11 is to illustrate use of the cyclotriveratrylene and derivatives thereof as an external electron donor in propylene polymerization catalyst.

Example 11

In this example, propylene polymerization was performed by using NDQ catalyst, which is available from Aoda Catalyst Company, SINOPEC, wherein Compound A was used as an external electron donor.

Propylene Polymerization Procedure

A 5 L autoclave was purged with nitrogen gas flow, and then under nitrogen atmosphere, 0.25 mmol of triethylaluminum, 0.01 mmol of external electron donor (Compound A), 10 ml of anhydrous hexane and 10 mg of the NDQ catalyst were introduced thereto. The autoclave was closed, and then 1.2 NL (standard volume) of hydrogen gas and 2.3 L of liquid propylene were introduced to the autoclave. The temperature inside the autoclave was brought to 70° C., and the polymerization was allowed to continue for 1.0 hours. Polymerization results are shown in Table 16 below.

Comparative Example 11

In this comparative example, propylene polymerization was performed by using NDQ catalyst, which is available from Aoda Catalyst Company, SINOPEC, wherein no Compound A was used as an external electron donor.

Propylene Polymerization Procedure

A 5 L autoclave was purged with nitrogen gas flow, and then under nitrogen atmosphere, 0.25 mmol of triethylaluminum, 10 ml of anhydrous hexane and 10 mg of the NDQ catalyst were introduced thereto. The autoclave was closed, and then 1.2 NL (standard volume) of hydrogen gas and 2.3 L of liquid propylene were introduced to the autoclave. The temperature inside the autoclave was brought to 70° C., and the polymerization was allowed to continue for 1.0 hours. Polymerization results are shown in Table 16 below.

TABLE 16

Propylene Polymerization results

| Example No. | External electron donor | Activity (kgPP/gCat) | Isotacticity (wt %) |
|---|---|---|---|
| Example 11 | Compound A | 53 | 97.9 |
| Comparative Example 11 | — | 60 | 95.1 |

It can be seen from Table 16 that the catalyst system provided by the present disclosure may be used for propylene polymerization, and compared to Comparative Example 11, in which no Compound A is added, Example 11 obtains a polymer having an enhanced isotacticity.

TABLE 1

Composition of solid catalyst components

| No. | Solid catalyst component | Ti (wt %) | Cyclotriveratrylene and derivatives thereof (wt %) |
|---|---|---|---|
| Example 1 | a | 5.3 | 2.0 |
| Comparative Example 1-1 | D1-1 | 7.4 | — |
| Comparative Example 1-2 | D1-2 | 3.8 | — |
| Example 2 | b | 6.0 | 1.8 |
| Comparative Example 2 | D2 | 6.3 | — |
| Example 3 | c | 6.2 | 1.5 |
| Comparative Example 3 | D3 | 6.5 | — |
| Example 4a | d1 | 3.2 | 1.2 |
| Example 4b | d2 | 3.0 | 1.0 |
| Comparative Example 4 | D4 | 2.8 | — |
| Example 5 | e | 3.0 | 2.0 |
| Comparative Example 5 | D5 | 2.6 | — |
| Example 8 | h | 6.5 | — |
| Example 9 | i | 2.5 | 0.5 |
| Comparative Example 9 | D9 | 2.4 | — |
| Example 10 | j | 2.6 | 0.8 |
| Comparative Example 10 | D10 | 2.8 | — |
| Example 11 | NDQ | 2.4 | — |

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein, but rather that the claims be construed as encompassing all the features of patentable novelty which reside herein, including all features which would be treated as equivalents thereof by those skilled in the art to which this disclosure pertains. The present disclosure has been described hereinabove by reference to many embodiments and specific examples. In view of the above detailed descriptions, many variations are apparent to those skilled in the art. All such variations are within the scope of the whole intention of the appended claims.

In the disclosure, whenever a composition, an element or a group of elements is preceded with the transitional phrase "comprising", it is understood that we also contemplate the same composition, element or group of elements with transitional phrases "consisting essentially of", "consisting of", "selected from the group consisting of", or "is" preceding the recitation of the composition, element, or elements and vice versa.

What is claimed is:

1. A Ziegler-Natta catalyst system for olefin polymerization, comprising at least one compound represented by formula (I) as (i) an internal electron donor, (ii) an external electron donor, or (iii) the both,

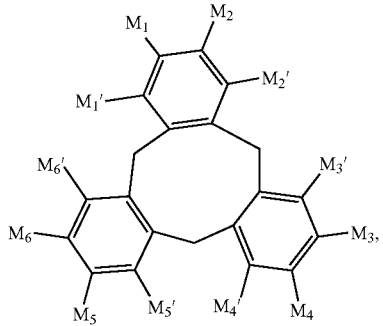

Formula (I)

wherein $M_1$, $M_2$, $M_3$, $M_4$, $M_5$, $M_6$, $M_1'$, $M_2'$, $M_3'$, $M_4'$, $M_5'$ and $M_6'$ are each independently selected from the group consisting of hydrogen, hydroxy, amino, aldehyde group, carboxy, acyl, halogen atoms, —$R_1$ and —$OR_2$, where $R_1$ and $R_2$ are each independently a $C_1$-$C_{10}$ hydrocarbyl, which is unsubstituted or substituted by a substituent selected from the group consisting of hydroxy, amino, aldehyde group, carboxy, acyl, halogen atoms, $C_1$-$C_{10}$ alkoxy and heteroatoms; and wherein, when among $M_1$-$M_6$ and $M_1'$-$M_6'$, any two adjacent groups on the same phenyl ring are each independently selected from the group consisting of $R_1$ and —$OR_2$, the two adjacent groups may optionally be linked to form a ring, with a proviso that $M_1$, $M_2$, $M_3$, $M_4$, $M_5$, $M_6$, $M_1'$, $M_2'$, $M_3'$, $M_4'$, $M_5'$ and $M_6'$ are not simultaneously hydrogen.

2. The catalyst system according to claim 1, wherein the compound represented by formula (I) is selected from those represented by formula (I'):

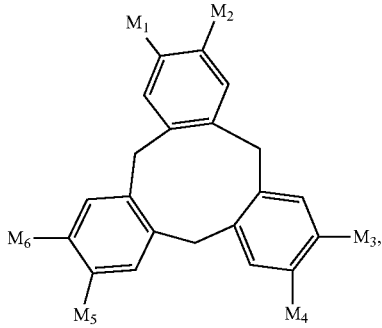

Formula (I')

wherein $M_1$, $M_2$, $M_3$, $M_4$, $M_5$ and $M_6$ are each independently selected from the group consisting of hydrogen, hydroxy, amino, aldehyde group, carboxy, acyl, halogen atoms, —$R_1$ and —$OR_2$, where $R_1$ and $R_2$ are each independently a $C_1$-$C_{10}$ hydrocarbyl, which is unsubstituted or substituted by a substituent selected from the group consisting of hydroxy, amino, aldehyde group, carboxy, acyl, halogen atoms, $C_1$-$C_{10}$ alkoxy and heteroatoms, with a proviso that when two adjacent groups on the same phenyl ring, i.e., $M_1$ and $M_2$, or $M_3$ and $M_4$, or $M_5$ and $M_6$, are each independently selected from the group consisting of —$R_1$ and —$OR_2$, the two adjacent groups may optionally be linked to form a ring, and further with a proviso that $M_1$, $M_2$, $M_3$, $M_4$, $M_5$ and $M_6$ are not simultaneously hydrogen.

3. The catalyst system according to claim 2, wherein in the formula (I'), $M_1$, $M_2$, $M_3$, $M_4$, $M_5$ and $M_6$ are each independently selected from the group consisting of hydroxy, amino, aldehyde group, halogen atoms, —$R_1$ and —$OR_2$, where $R_1$ and $R_2$ are each independently selected from the group consisting of unsubstituted or halogen-substituted $C_1$-$C_{10}$ hydrocarbyl groups.

4. The catalyst system according to claim 1, wherein the at least one compound represented by formula (I) is selected from the group consisting of:

Compound A: $M_1=M_2=M_3=M_4=M_5=M_6=OCH_3$, $M_1'=M_2'=M_3'=M_4'=M_5'=M_6'=H$;

Compound B: $M_1=M_2=M_3=M_4=M_5=M_6=OCH_2CH_3$, $M_1'=M_2'=M_3'=M_4'=M_5'=M_6'=H$ Compound C: $M_1=M_2=M_3=M_4=M_5=M_6=OCH_2CH_2CH_3$, $M_1'=M_2'=M_3'=M_4'=M_5'=M_6'=H$;

Compound D: $M_1=M_2=M_3=M_4=M_5=M_6=OCH(CH_3)_2$, $M_1'=M_2'=M_3'=M_4'=M_5'=M_6'=H$;

Compound E: $M_1=M_2=M_3=M_4=M_5=M_6=OCH_2CH_2CH_2CH_3$, $M_1'=M_2'=M_3'=M_4'=M_5'=M_6'=H$;

Compound F: $M_1=M_3=M_5=OCH_3$, $M_2=M_4=M_6=OCH_2CH_3$, $M_1'=M_2'=M_3'=M_4'=M_5'=M_6'=H$;

Compound G: $M_1=M_3=M_5=OCH_3$, $M_2=M_4=M_6=OCH_2CH_2CH_3$, $M_1'=M_2'=M_3'=M_4'=M_5'=M_6'=H$;

Compound H: $M_1=M_3=M_5=OCH_3$, $M_2=M_4=M_6=OCH_2CH_2CH_2CH_3$, $M_1'=M_2'=M_3'=M_4'=M_5'=M_6'=H$;

Compound I: $M_1=M_2=M_3=M_4=M_5=M_6=OH$, $M_1'=M_2'=M_3'=M_4'=M_5'=M_6'=H$;

Compound J: $M_1=M_3=M_5=OCH_3$, $M_2=M_4=M_6=OH$, $M_1'=M_2'=M_3'=M_4'=M_5'=M_6'=H$;

Compound K: $M_1=M_3=M_5=OCH_3$, $M_2=M_4=M_6=NH_2$, $M_1'=M_2'=M_3'=M_4'=M_5'=M_6'=H$;

Compound L: $M_1=M_3=M_5=OCH_3$, $M_2=M_4=M_6=Cl$, $M_1'=M_2'=M_3'=M_4'=M_5'=M_6'=H$;

Compound M: $M_1=M_3=M_5=OCH_3$, $M_2=M_4=M_6=Br$, $M_1'=M_2'=M_3'=M_4'=M_5'=M_6'=H$;

Compound N: $M_1=M_3=M_5=OCH_3$, $M_2=M_4=M_6=I$, $M_1'=M_2'=M_3'=M_4'=M_5'=M_6'=H$;

Compound O: $M_1=M_3=M_5=OCH_3$, $M_2=M_4=M_6=CHO$, $M_1'=M_2'=M_3'=M_4'=M_5'=M_6'=H$;

Compound P: $M_1=M_3=M_5=OCH_3$, $M_2=M_4=M_6=OCH_2CH_2CH_2Br$, $M_1'=M_2'=M_3'=M_4'=M_5'=M_6'=H$;

Compound Q: $M_1=M_2=M_3=M_4=M_5=M_6=OCH_2CH_2Cl$, $M_1'=M_2'=M_3'=M_4'=M_5'=M_6'=H$;

Compound R: $M_1=M_3=M_5=OH$, $M_2=M_4=M_6=OCH_2CH_3$, $M_1'=M_2'=M_3'=M_4'=M_5'=M_6'=H$;

Compound S: $M_1=M_2=M_3=M_4=M_5=M_6=OCH_3$, $M_1'=Cl$, $M_2'=M_3'=M_4'=M_5'=M_6'=H$;

Compound T: $M_1=M_2=M_3=M_4=M_5=M_6=OCH_3$, $M_1'=M_3'=Cl$, $M_2'=M_4'=M_5'=M_6'=H$;

Compound U: $M_1=M_2=M_3=M_4=M_5=M_6=OCH_3$, $M_1'=M_3'=M_5'=Cl$, $M_2'=M_4'=M_6'=H$; and Compound V: $M_1=M_2=M_3=M_4=M_5=M_6=OCH_3$, $M_1'=M_3'=M_6'=Cl$, $M_2'=M_4'=M_5'=H$.

5. A solid catalyst component for olefin polymerization, comprising magnesium, titanium, halogen and an internal electron donor compound, wherein the internal electron donor compound comprises at least one compound of the formula (I) as defined in claim 1.

6. The solid catalyst component according to claim 5, comprising at least one titanium compound and the at least one compound represented by formula (I), supported on a magnesium halide.

7. The solid catalyst component according to claim 5, wherein a molar ratio of the at least one compound represented by formula (I) to magnesium ranges from 0.0005:1 to 0.1:1, or from 0.001:1 to 0.1:1, or from 0.002:1 to 0.05:1.

8. The solid catalyst component according to claim 6, wherein the at least one titanium compound is selected from the group consisting of titanium trichloride and those having general formula $Ti(OR)_nX'_{4-n}$, where R is a $C_1$-$C_8$ hydrocarbyl, X' is a halogen atom, and $0 \leq n \leq 4$; or the at least one titanium compound is selected from the group consisting of titanium trichloride, titanium tetrachloride, titanium tetrabromide, tetraethoxy titanium, triethoxy titanium chloride, diethoxy titanium dichloride, tetrabutoxy titanium and ethoxy titanium trichloride.

9. The solid catalyst component according to claim 5, comprising a reaction product of:
   1) a magnesium halide-alcohol adduct;
   2) a titanium compound;
   3) an internal electron donor compound; and
   4) optionally, an organic aluminum compound,
   wherein the internal electron donor compound comprises the at least one compound represented by formula (I).

10. The solid catalyst component according to claim 9, having at least one feature of the followings:
    the organic aluminum compound is of general formula $AlR^1_aX^1_bH_c$, where $R^1$ is a $C_1$-$C_{14}$ hydrocarbyl; $X^1$ is a halogen atom; a, b and c are each a number of from 0 to 3; and a+b+c=3;
    the content of the at least one compound represented by formula (I) is at least 0.0005 moles, or at least 0.001 moles, or from 0.001 to 0.1 moles, relative to one mole of magnesium;
    the magnesium halide-alcohol adduct is of general formula $MgX_2 \cdot m(ROH)$, where X is Cl, Br or I; R is a $C_1$-$C_6$ alkyl; and m ranges from 0.5 to 4.0, or from 2.5 to 4.0;
    the titanium compound is of general formula $Ti(OR^2)_n X^2_{4-n}$, where $R^2$ is a $C_1$-$C_8$ hydrocarbyl; $X^2$ is Cl, Br or I; and $0 \leq n \leq 4$; or the titanium compound is selected from the group consisting of $TiCl_4$, $Ti(OC_2H_5)Cl_3$, $Ti(OCH_3)Cl_3$, $Ti(OC_4H_9)Cl_3$, $Ti(OC_4H_9)_4$ and mixtures thereof; and
    in a reaction for forming the solid catalyst component, relative to one mole of magnesium, the amount of the titanium compound used ranges from 0.1 to 100 moles, or from 1 to 50 moles, and the amount of the organic aluminum compound used ranges from 0 to 5 moles.

11. The solid catalyst component according to claim 5, comprising a reaction product of:
    1) an alkoxy magnesium compound;
    2) a titanium compound; and
    3) an internal electron donor compound;
    wherein the internal electron donor compound comprises the at least one compound represented by formula (I).

12. The solid catalyst component according to claim 11, having at least one feature of the followings:
    the content of the at least one compound represented by formula (I) is at least 0.0005 moles, or at least 0.001 moles, or in a range of from 0.001 to 0.1 moles, relative to one mole of magnesium;
    the alkoxy magnesium compound is of general formula $Mg(OR_3)_a(OR_4)_{2-a}$, where $R_3$ and $R_4$ are each independently selected from the group consisting of $C_1$-$C_{10}$ hydrocarbyl groups, which are unsubstituted or substituted by a substituent selected from the group consisting of hydroxy, amino, aldehyde group, carboxy, acyl, halogen atoms, alkoxy and heteroatoms, and $0 \leq a \leq 2$;
    the titanium compound is of general formula $Ti(OR)_n X_{4-n}$, where R is a $C_1$-$C_8$ hydrocarbyl; X is a halogen atom; and $0 \leq n \leq 4$; or the titanium compound is selected from the group consisting of $TiCl_4$, $Ti(OC_2H_5)Cl_3$, $Ti(OCH_3)Cl_3$, $Ti(OC_4H_9)Cl_3$, $Ti(OC_4H_9)_4$ and mixtures thereof;
    in a reaction for forming the solid catalyst component, relative to one mole of magnesium, the amount of the titanium compound used ranges from 0.1 to 100 moles, or from 1 to 50 moles;
    the solid catalyst component is prepared by a process comprising: dispersing the alkoxy magnesium compound in an inert solvent to afford a suspension; contacting the suspension with the titanium compound and the at least one compound represented by formula (I) to obtain a contacted product; and further reacting the contacted product with the titanium compound to afford the solid catalyst component,
    alternatively, the solid catalyst component is prepared by a process comprising: dispersing the alkoxy magnesium compound in an inert solvent to afford a suspension; contacting the suspension with the titanium compound to obtain a contacted product; and further reacting the contacted product with the titanium compound and the at least one compound represented by formula (I) to afford the solid catalyst component.

13. The solid catalyst component according to claim 5, comprising a reaction product of:
    1) a finely-divided support having a particle size of from 0.01 to 10 microns;
    2) a magnesium halide;
    3) a titanium halide; and
    4) an internal electron donating compound, which comprises an internal electron donor a and an internal electron donor b,
    wherein the internal electron donor a is the at least one compound represented by formula (I), and the internal electron donor b is at least one selected from the group consisting of alkyl esters of $C_2$-$C_{10}$ saturated aliphatic carboxylic acids, alkyl esters of $C_7$-$C_{10}$ aromatic carboxylic acids, $C_2$-$C_{10}$ aliphatic ethers, $C_3$-$C_{10}$ cyclic ethers, and $C_3$-$C_{10}$ saturated aliphatic ketones; and
    wherein a molar ratio of the titanium halide to the internal electron donor a ranges from 5:1 to 2000:1, and a molar ratio of the titanium halide to the internal electron donor b ranges from 1:1 to 1:600.

14. The solid catalyst component according to claim 13, having at least one feature of the followings:
    the internal electron donor b is at least one selected from the group consisting of methyl formate, ethyl acetate, butyl acetate, diethyl ether, dihexyl ether, tetrahydrofuran, acetone and methyl isobutyl ketone;
    the magnesium halide is at least one selected from the group consisting of $MgCl_2$, $MgBr_2$ and $MgI_2$;
    the titanium halide is at least one selected from the group consisting of titanium tetrachloride and titanium trichloride;
    the finely-divided support is at least one selected from the group consisting of alumina, activated carbon, clays, silica, titania, polystyrenes and calcium carbonate; and
    the solid catalyst component is prepared by a process comprising: mixing the magnesium halide, the titanium halide, the internal electron donor a and the internal electron donor b and allowing the resultant mixture to react at 0 to 90° C. for 0.5 to 5 hours to afford a mother liquor; at 0 to 90° C., mixing the mother liquor with the finely-divided support and stirring the resultant mixture for 0.5 to 3 hours to afford a finely-divided support-admixed mother liquor; and spray-drying the finely-divided support-admixed mother liquor to obtain the solid catalyst component, wherein a content of the finely-divided support in the finely-divided support-admixed mother liquor ranges from 3 to 50 wt. %, or from 10 to 30 wt. %.

15. The solid catalyst component according to claim 5, comprising a reaction product of:
   1) a magnesium-containing liquid-state component, which is at least one selected from the following components:
      i) an alkyl magnesium or a solution thereof in a liquid hydrocarbon, the alkyl magnesium being of general formula $MgR_1R_2$, where $R_1$ and $R_2$ are each independently selected from the group consisting of $C_1$-$C_{10}$ hydrocarbyl groups, which are unsubstituted or substituted by a substituent selected from the group consisting of hydroxy, amino, aldehyde group, carboxy, halogen atoms, alkoxy and heteroatoms;
      ii) a product obtained by dissolving, in a solvent system comprising an organophosphorus compound, an organic epoxy compound and an optional alcohol compound $R_5OH$, a magnesium dihalide or a derivative deriving from a magnesium dihalide by replacing one halogen atom in the molecular formula of the magnesium dihalide with group $R_3$ or $OR_4$; and
      iii) a product obtained by dispersing, in an alcohol compound $R_5OH$, a magnesium dihalide or a derivative deriving from a magnesium dihalide by replacing one halogen atom in the molecular formula of the magnesium dihalide with group $R_3$ or $OR_4$;
      where $R_3$, $R_4$ and $R_5$ are each independently selected from the group consisting of $C_1$-$C_{10}$ hydrocarbyl groups, which are unsubstituted or substituted by a substituent selected from the group consisting of hydroxy, amino, aldehyde group, carboxy, halogen atoms, alkoxy and heteroatoms;
   2) a titanium compound;
   3) an internal electron donor compound; and
   4) optionally, an auxiliary precipitant, which is selected from the group consisting of organic anhydride compounds and/or organic silicon compounds,
   wherein the internal electron donor compound comprises the at least one compound represented by formula (I).

16. The solid catalyst component according to claim 15, having at least one feature of the followings:
   the alkyl magnesium is at least one selected from the group consisting of dimethyl magnesium, diethyl magnesium, n-butyl ethyl magnesium, di-n-butyl magnesium, and butyl octyl magnesium;
   the magnesium dihalide or derivative deriving from a magnesium dihalide by replacing one halogen atom in the molecular formula of the magnesium dihalide with group $R_3$ or $OR_4$ is at least one selected from the group consisting of $MgCl_2$, $MgBr_2$, $MgI_2$, $MgCl(OCH_2CH_3)$, $MgCl(OBu)$, $CH_3MgCl$ and $CH_3CH_2MgCl$;
   the organophosphorus compound is selected from the group consisting of hydrocarbyl esters and halogenated hydrocarbyl esters of ortho-phosphoric acid, and hydrocarbyl esters and halogenated hydrocarbyl esters of phosphorous acid, or the organophosphorus compound is at least one selected from the group consisting of triethyl phosphate, tributyl phosphate, tri-isooctyl phosphate, triphenyl phosphate, triethyl phosphite, tributyl phosphite and di-n-butyl phosphite;
   the organic epoxy compound is at least one selected from the group consisting of aliphatic epoxy compounds and diepoxy compounds, halogenated aliphatic epoxy compounds and diepoxy compounds, glycidyl ethers, and inner ethers, having from 2 to 18 carbon atoms, or is at least one selected from the group consisting of epoxy ethane, epoxy propane, epoxy butane, vinyl epoxy ethane, epoxy chloropropane, glycidyl methacrylate, glycidyl ethyl ether and glycidyl butyl ether;
   the alcohol compound is at least one selected from the group consisting of methanol, ethanol, propanol, iso-propanol, butanol, isobutanol, tert-butanol, hexanol, cyclohexanol, octanol, isooctanol, decanol, benzyl alcohol and phenylethanol;
   the titanium compound is of general formula $Ti(OR_6)_n X_{4-n}$, where $R_6$ is a $C_1$-$C_8$ hydrocarbyl, X is a halogen atom, and $0 \le n \le 3$; or the titanium compound is at least one selected from the group consisting of $TiCl_4$, $TiBr_4$, $TiI_4$, $Ti(OC_2H_5)Cl_3$, $Ti(OCH_3)Cl_3$, $Ti(OC_4H_9)Cl_3$, $Ti(OC_2H_5)Br_3$, $Ti(OC_2H_5)_2Cl_2$, $Ti(OCH_3)_2Cl_2$, $Ti(OCH_3)_2I_2$, $Ti(OC_2H_5)_3Cl$, $Ti(OCH_3)_3Cl$ and $Ti(OC_2H_5)_3I$;
   the organic anhydride compounds are represented by formula (II): $R^1CO\text{—}O\text{—}CO\text{—}R^2$ (II), where $R^1$ and $R^2$ are each independently selected from the group consisting of hydrogen and $C_1$-$C_{10}$ hydrocarbyl groups, and $R^1$ and $R^2$ may optionally be linked to form a ring;
   the organic silicon compounds are of general formula $R^3_x R^4_y Si(OR^5)_z$, where $R^3$ and $R^4$ are each independently selected from the group consisting of $C_1$-$C_{10}$ hydrocarbyl groups and halogen atoms; $R^5$ is a $C_1$-$C_{10}$ hydrocarbyl; each x, y and z is a positive integer, $0 \le x \le 2$, $0 \le y \le 2$, $0 \le z \le 4$, and $x+y+z=4$;
   in a reaction for forming the solid catalyst component, relative to one mole of magnesium, the amount of the titanium compound used ranges from 0.5 to 120 moles, or from 1 to 50 moles; and the amount of the at least one compound represented by formula (I) used ranges from 0.0005 to 1 mole, or from 0.001 to 1 mole, or from 0.001 to 0.05 moles.

17. A catalyst system for olefin polymerization, comprising a reaction product of:
   1) the solid catalyst component according to claim 5;
   2) a cocatalyst; and
   3) an optional external electron donor compound.

18. The catalyst system according to claim 17, wherein the cocatalyst is at least one organic aluminum compound represented by general formula $AlR^1_d X^1_{3-d}$, where $R^1$ is hydrogen or a $C_1$-$C_{20}$ hydrocarbyl, $X^1$ is a halogen atom, and $0 \le d \le 3$, and a molar ratio of aluminum in the cocatalyst to titanium in the solid catalyst component ranges from 5:1 to 500:1, or from 20:1 to 200:1.

19. A catalyst system for olefin polymerization, comprising a reaction product of:
   1) a solid catalyst component comprising magnesium, titanium, halogen and an optional internal electron donor compound;
   2) a cocatalyst; and
   3) an external electron donor compound, which comprises at least one compound of the formula (I) as defined in claim 1.

20. The catalyst system according to claim 19, wherein the solid catalyst component comprises at least one titanium compound having at least one Ti-halogen bond, supported on a magnesium halide.

21. The catalyst system according to claim 20, wherein the at least one titanium compound is selected from the group consisting of titanium trihalides and compounds represented by general formula $Ti(OR^2)_n X^2_{4-n}$, where $R^2$ is a $C_1$-$C_8$ hydrocarbyl; $X^2$ is Cl, Br or I; and $0 \leq n \leq 4$; or the at least one titanium compound is selected from the group consisting of $TiCl_3$, $TiCl_4$, $TiBr_4$, $Ti(OC_2H_5)Cl_3$, $Ti(OC_2H_5)_2 Cl_2$ and $Ti(OC_2H_5)_3Cl$.

22. The catalyst system according to claim 19, having at least one feature of the followings:
the cocatalyst is at least one organic aluminum compound represented by general formula $AlR^1_d X^1_{3-d}$, where $R^1$ is hydrogen or a $C_1$-$C_{20}$ hydrocarbyl, $X^1$ is a halogen atom, and $0 \leq d \leq 3$, and a molar ratio of aluminum in the cocatalyst to titanium in the solid catalyst component ranges from 5:1 to 500:1, or from 20:1 to 200:1;
a molar ratio of the external electron donor compound to titanium in the solid catalyst component ranges from 0.05:1 to 50:1.

23. The catalyst system according to claim 19, wherein the solid catalyst component comprises a reaction product of: a magnesium halide-alcohol adduct, a titanium compound, an optional internal electron donor compound and an optional second organic aluminum compound, the second organic aluminum compound being of general formula $AlR^3_a X^3_b H_c$, where $R^3$ is a $C_1$-$C_{14}$ hydrocarbyl; $X^3$ is a halogen atom; each a, b and c is a number of from 0 to 3, and a+b+c=3.

24. The catalyst system according to claim 23, having at least one feature of the followings:
the magnesium halide-alcohol adduct is of general formula $MgX_2 \cdot m(ROH)$, where X is Cl, Br or I; R is a $C_1$-$C_6$ alkyl; and m is from 0.5 to 4.0, or from 2.5 to 4.0;
the titanium compound is of general formula $Ti(OR^2)_n X^2_{4-n}$, where $R^2$ is a $C_1$-$C_8$ hydrocarbyl; $X^2$ is Cl, Br or I; and $0 \leq n \leq 4$; or the titanium compound is selected from the group consisting of $TiCl_4$, $Ti(OC_2H_5)Cl_3$, $Ti(OCH_3)Cl_3$, $Ti(OC_4H_9)Cl_3$, $Ti(OC_4H_9)_4$ and mixtures thereof;
the second organic aluminum compound is selected from the group consisting of $Al(CH_2CH_3)_3$, $Al(i-Bu)_3$, $Al(n-C_6H_{13})_3$ and mixtures thereof;
in a reaction for forming the solid catalyst component, relative to one mole of magnesium, the amount of the titanium compound used ranges from 1 to 50 moles; the amount of the internal electron donor compound used ranges from 0 to 1 mole; and the amount of the second organic aluminum compound used ranges from 0 to 100 moles.

25. The catalyst system according to claim 19, wherein the solid catalyst component comprises a reaction product of: an alkoxy magnesium compound, a titanium compound and an optional internal electron donor compound.

26. The catalyst system according to claim 25, having at least one feature of the followings:
the alkoxy magnesium compound is of general formula $Mg(OR_3)_a(OR_4)_{2-a}$, where $R_3$ and $R_4$ are each independently a $C_1$-$C_{10}$ alkyl, which is unsubstituted or substituted by a substituent selected from the group consisting of hydroxy, amino, aldehyde group, carboxy, acyl, halogen atoms, alkoxy and heteroatoms, and $0 \leq a \leq 2$;
the titanium compound is of general formula $Ti(OR^2)_n X^2_{4-n}$, where $R^2$ is a $C_1$-$C_8$ hydrocarbyl; $X^2$ is Cl, Br or I; and $0 \leq n \leq 4$; or the titanium compound is selected from the group consisting of $TiCl_4$, $Ti(OC_2H_5)Cl_3$, $Ti(OCH_3)Cl_3$, $Ti(OC_4H_9)Cl_3$, $Ti(OC_4H_9)_4$ and mixtures thereof;
in a reaction for forming the solid catalyst component, relative to one mole of magnesium, the amount of the titanium compound used ranges from 0.1 to 15 moles; and the amount of the internal electron donor compound used ranges from 0 to 0.1 moles.

27. The catalyst system according to claim 19, wherein the solid catalyst component comprises a reaction product of: a finely-divided support, a magnesium halide, a titanium halide, an internal electron donor b and an optional internal electron donor a, wherein the internal electron donor b is at least one selected from the group consisting of alkyl esters of $C_2$-$C_{10}$ saturated aliphatic carboxylic acids, alkyl esters of $C_7$-$C_{10}$ aromatic carboxylic acids, $C_2$-$C_{10}$ aliphatic ethers, $C_3$-$C_{10}$ cyclic ethers and $C_3$-$C_{10}$ saturated aliphatic ketones, and wherein the optional internal electron donor a is at least one compound represented by the formula (I).

28. The catalyst system according to claim 27, having at least one feature of the followings:
the finely-divided support is selected from the group consisting of alumina, activated carbon, clays, silica, titania, polystyrenes, calcium carbonate and mixtures thereof, and the finely-divided support has a particle size of from 0.01 to 10 μm;
the magnesium halide is selected from the group consisting of $MgCl_2$, $MgBr_2$, $MgI_2$ and mixtures thereof;
the titanium halide is $TiCl_3$ and/or $TiCl_4$;
the solid catalyst component is prepared by a process comprising: combining the magnesium halide, the titanium halide, the internal electron donor b and the optional internal electron donor a to obtain a mother liquor; admixing the finely-divided support with the mother liquor to obtain a slurry; and spray-drying the slurry to afford the solid catalyst component, wherein a content of the finely-divided support in the slurry ranges from 3 to 50 wt %, or from 5 to 30 wt %;
a molar ratio of the titanium halide to the magnesium halide ranges from 1:20 to 1:2;
a molar ratio of the titanium halide to the internal electron donor b ranges from 1:1 to 1:600.

29. The catalyst system according to claim 19, wherein the solid catalyst component comprises a reaction product of: a magnesium-containing liquid-state component, a titanium compound, an optional internal electron donor compound and an optional auxiliary precipitant, wherein the auxiliary precipitant is selected from the group consisting of organic anhydride compounds and organic silicon compounds.

30. The catalyst system according to claim 29, having at least one feature of the followings:
the magnesium-containing liquid-state component is at least one selected from the group consisting of:
Component A: an alkyl magnesium compound of general formula $MgR_3R_4$;
Component B: a reaction product of a magnesium compound, an organophosphorus compound, an organic epoxy compound and an optional alcohol compound of general formula $R_7OH$;
Component C: a reaction product of a magnesium compound and an alcohol compound of general formula $R_7OH$, wherein the magnesium compound is of general formula $MgX^3_m R^3_{2-m}$, where $X^3$ is halogen, $R^3$ is —$R_5$ or —$OR_6$, m=1 or 2; $R_3$, $R_4$, $R_5$, $R_6$ and $R_7$ are each independently a hydrocarbyl, which is unsubstituted or substituted by a substituent selected from the group consisting of hydroxy, amino, aldehyde group, carboxy, halogen atoms, alkoxy and heteroatoms;

the organophosphorus compound is selected from the group consisting of hydrocarbyl esters and halogenated hydrocarbyl esters of ortho-phosphoric acid, and hydrocarbyl esters and halogenated hydrocarbyl esters of phosphorous acid, or the organophosphorus compound is at least one selected from the group consisting of triethyl phosphate, tributyl phosphate, tri-isooctyl phosphate, triphenyl phosphate, triethyl phosphite, tributyl phosphite and di-n-butyl phosphite;

the organic epoxy compound is at least one selected from the group consisting of aliphatic epoxy compounds and diepoxy compounds, halogenated aliphatic epoxy compounds and diepoxy compounds, glycidyl ethers, and inner ethers, having from 2 to 18 carbon atoms, or is at least one selected from the group consisting of epoxy ethane, epoxy propane, epoxy butane, vinyl epoxy ethane, epoxy chloropropane, glycidyl methacrylate, glycidyl ethyl ether and glycidyl butyl ether;

the alcohol compound of the general formula $R_7OH$ is at least one selected from the group consisting of methanol, ethanol, propanol, isopropanol, butanol, isobutanol, tert-butanol, hexanol, cyclohexanol, octanol, isooctanol, decanol, benzyl alcohol and phenylethanol;

the titanium compound is of general formula $Ti(OR^2)_n X^2_{4-n}$, where $R^2$ is a $C_1$-$C_8$ hydrocarbyl; $X^2$ is Cl, Br or I; and $0 \leq n \leq 4$; or the titanium compound is selected from the group consisting of $TiCl_4$, $Ti(OC_2H_5)Cl_3$, $Ti(OCH_3)Cl_3$, $Ti(OC_4H_9)Cl_3$ and mixtures thereof;

the organic anhydride compound is at least one selected from those represented by formula (II): $R^1$CO—O—CO—$R_2$ (II), wherein $R^4$ and $R^5$ are each independently selected from the group consisting of hydrogen, $C_1$-$C_{10}$ alkyl, $C_2$-$C_{10}$ alkenyl, $C_2$-$C_{10}$ alkynyl, $C_3$-$C_8$ cycloalkyl and $C_6$-$C_{10}$ aromatic hydrocarbyl, and $R^4$ and $R^5$ may optionally be linked to form a ring;

the organic silicon compound is of general formula $R^6_x R^7_y Si(OR^8)_z$, where $R^6$ and $R^7$ are each independently a $C_1$-$C_{10}$ hydrocarbyl or halogen, $R^8$ is a $C_1$-$C_{10}$ hydrocarbyl, each x, y and z is an integer, $0 \leq x \leq 2$, $0 \leq y \leq 2$, $0 \leq z \leq 4$, and x+y+z=4;

in a reaction for forming the solid catalyst component, relative to one mole of magnesium, the amount of the titanium compound used ranges from 0.5 to 120 moles, or from 1 to 50 moles; the amount of the internal electron donor compound used ranges from 0 to 0.1 moles, or from 0 to 0.05 moles; and the amount of the auxiliary precipitant used ranges from 0 to 1 mole, or from 0 to 0.7 moles.

31. An olefin polymerization process comprising: contacting an olefin monomer and an optional comonomer with the catalyst system according to claim 1 under polymerization conditions to form a polyolefin product and recovering the polyolefin product.

32. An olefin polymerization process comprising: contacting an olefin monomer and an optional comonomer with the catalyst system according to claim 17 under polymerization conditions to form a polyolefin product and recovering the polyolefin product.

33. An olefin polymerization process comprising: contacting an olefin monomer and an optional comonomer with the catalyst system according to claim 19 under polymerization conditions to form a polyolefin product and recovering the polyolefin product.

\* \* \* \* \*

UNITED STATES PATENT AND TRADEMARK OFFICE
CERTIFICATE OF CORRECTION

PATENT NO. : 11,401,356 B2
APPLICATION NO. : 16/631482
DATED : August 2, 2022
INVENTOR(S) : Ting Huang et al.

It is certified that error appears in the above-identified patent and that said Letters Patent is hereby corrected as shown below:

In the Claims

Claim 21, Column 51, Line 13, "$Ti(OC_2H_5)_2\ Cl_2$" should read as --$Ti(OC_2H_5)_2Cl_2$--.

Signed and Sealed this
Eighteenth Day of October, 2022

Katherine Kelly Vidal
*Director of the United States Patent and Trademark Office*